(12) United States Patent
Greaves et al.

(10) Patent No.: US 7,208,586 B2
(45) Date of Patent: Apr. 24, 2007

(54) CATIONIC DIAZO COMPOUNDS, COMPOSITIONS COMPRISING THEM AS DIRECT DYE, PROCESS FOR DYEING KERATIN FIBERS AND DEVICE THEREFOR

(75) Inventors: Andrew Greaves, Montevrain (FR); Hervé David, La Varenne Saint Hilaire (FR)

(73) Assignee: L'Oreal S.A., Paris (FR)

( * ) Notice: Subject to any disclaimer, the term of this patent is extended or adjusted under 35 U.S.C. 154(b) by 64 days.

(21) Appl. No.: 11/159,267

(22) Filed: Jun. 23, 2005

(65) Prior Publication Data

US 2006/0016025 A1  Jan. 26, 2006

Related U.S. Application Data

(60) Provisional application No. 60/588,047, filed on Jul. 15, 2004.

(30) Foreign Application Priority Data

Jun. 23, 2004  (FR)  ................... 04 06872

(51) Int. Cl.
*C09B 44/12*   (2006.01)
*C09B 44/16*   (2006.01)
*A61Q 5/10*   (2006.01)

(52) U.S. Cl. .............................. 534/608; 8/405; 8/406; 8/408; 8/426

(58) Field of Classification Search ............... 534/608; 8/405, 406, 408, 426
See application file for complete search history.

(56) References Cited

U.S. PATENT DOCUMENTS

| | | | |
|---|---|---|---|
| 3,151,106 A | 9/1964 | Tsang et al. |
| 4,003,699 A | 1/1977 | Rose et al. |
| RE30,199 E | 1/1980 | Rose et al. |
| 4,563,191 A | 1/1986 | Hähnke et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 5,792,221 A | 8/1998 | Lagrange et al. |
| 5,852,179 A | 12/1998 | Dado |
| 6,099,593 A | 8/2000 | Terranova et al. |
| 6,284,003 B1 | 9/2001 | Rose et al. |
| 6,645,258 B2 | 11/2003 | Vidal et al. |
| 6,884,265 B2 | 4/2005 | Vidal et al. |
| 2004/0244124 A1 | 12/2004 | Plos et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 044 059 | 1/1982 |
| EP | 0 714 954 | 6/1996 |
| EP | 0 770 375 | 5/1997 |
| WO | WO 02/100366 | 12/2002 |

OTHER PUBLICATIONS

Erwin Buncel and Sam-Rok Keum, "Studies of Azo and Azoxy Dyestuffs—16. Investigations of the Protonation and Tautomeric Equilibria of 4-(p'-Hydroxyphenylazo)pyridine and Related Substrates," Tetrahedron, vol. 39, No. 7, pp. 1091-1101 (1983).
English language DERWENT abstract of EP 0 770 375.
English language DERWENT abstract of JP 2-19576.
English language DERWENT abstract of JP 5-163124.
French Search Report dated Feb. 15, 2005, for FR 0406872 (French Priority Application for U.S. Appl. No. 11/159,267, the present application).

(Continued)

*Primary Examiner*—Fiona T. Powers
(74) *Attorney, Agent, or Firm*—Finnegan, Henderson, Farabow, Garrett & Dunner L.L.P.

(57) ABSTRACT

Disclosed are cationic diazo compounds of the following formula

Dye1-LK-Dye2   (I)

in which Dye1 and Dye2 represent:

Dye 1:

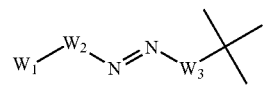

Dye 2:

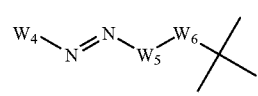 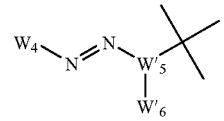

Also herein disclosed are dye compositions comprising the cationic diazo compounds as direct dye, a process for dyeing keratin fibers using this composition, and a multi-compartment device.

50 Claims, No Drawings

OTHER PUBLICATIONS

French Search Report dated Feb. 16, 2005, for FR 0406871 (French Priority Application for co-pending U.S. Appl. No. 11/159,154).

French Search Report dated Feb. 16, 2005, for FR 0406870 (French Priority Application for co-pending U.S. Appl. No. 11/159,242).

French Search Report dated Feb. 16, 2005, for FR 0406869 (French Priority Application for co-pending U.S. Appl. No. 11/159,237).

Co-pending U.S. Appl. No. 11/159,154, Title: A Cationic Diazo Compound, Compositions Comprising at Least One Cationic Diazo Compound as Direct Dye, A Process for Dyeing Keratin Fibers and Device Therefor, Inventors: Andrew Greaves et al., filed Jun. 23, 2005.

Co-pending U.S. Appl. No. 11/159,242, Title: Cationic Diazo Compounds, Compositions Comprising Them as Direct Dye, Process for Dyeing Keratin Fibers and Device Therefor, Inventors: Andrew Greaves et al., filed Jun. 23, 2005.

Co-pending U.S. Appl. No. 11/159,237, Title: Cationic Diazo Compounds, Compositions Comprising Them as Direct Dye, Procss for Dyeing Keratin Fibers and Device Therefor, Inventors: Andrew Greaves et al., filed Jun. 23, 2005.

CATIONIC DIAZO COMPOUNDS, COMPOSITIONS COMPRISING THEM AS DIRECT DYE, PROCESS FOR DYEING KERATIN FIBERS AND DEVICE THEREFOR

This application claims benefit of U.S. Provisional Application No. 60/588,047, filed Jul. 15, 2004, the contents of which are incorporated herein by reference. This application also claims benefit of priority under 35 U.S.C. § 119 to French Patent Application No. 04 06872, filed Jun. 23, 2004, the contents of which are also incorporated by reference.

Disclosed herein are cationic diazo compounds, dye compositions comprising such compounds as direct dye in a medium that is suitable for dyeing keratin fibers, and also a process for dyeing keratin fibers using this composition and a multi-compartment device.

It is known practice to dye keratin fibers, for example, human keratin fibers such as the hair, with dye compositions containing direct dye compounds. These compounds may be colored and coloring molecules with affinity for the fibers. It is known practice, for example, to use nitrobenzene direct dyes, anthraquinone dyes, nitropyridine dyes, azo dyes, xanthene dyes, acridine dyes, azine dyes, and triarylmethane dyes.

These dyes may be applied to the fibers, optionally in the presence of an oxidizing agent if it is desired to obtain simultaneous lightening of the fibers. Once the leave-in time has elapsed, the fibers are rinsed, and optionally washed and dried.

The colorations resulting from the use of direct dyes may be temporary or semi-permanent colorations since the nature of the interactions that bind the direct dyes to the keratin fiber, and their desorption from the surface and/or the core of the fiber, may be responsible for their poor dyeing power and their poor relative resistance to washing and/or to perspiration.

An additional difficulty may also arise, associated with the fact that in order to obtain a color, it is necessary in many cases to mix together several dyes. However, each dye may not have the same affinity for the fibers, which may be reflected by heterogeneous colorations and/or by changes in color over time, for example after washing the fibers, exposure to sunlight, etc.

One embodiment disclosed herein is providing at least one direct dye that may not have one or more of the drawbacks of existing direct dyes.

For example, embodiments of the present disclosure provide direct dyes with which varied shades may be obtained without the problem of changing in color over time.

Disclosed herein are cationic diazo compounds of formula (I) below, or the acid addition salts thereof:

Dye1-LK-Dye2    (I)

in which Dye1 and Dye2 represent:

Dye 1:

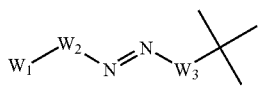

Dye 2:

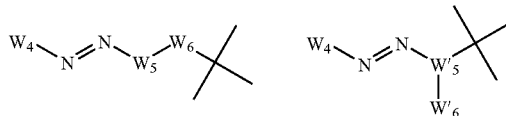

in which formulae:

$W_1$ and $W'_6$, independently of each other, are chosen from —$NR_1R_2$ and —$OR_3$, in which $R_1$, $R_2$, and $R_3$, independently of each other, are chosen from hydrogen and saturated or unsaturated, aromatic or non-aromatic, optionally substituted $C_1$–$C_{20}$ hydrocarbon-based chains, for example, $C_1$–$C_{16}$ hydrocarbon-based chains, which may form at least one optionally substituted 3- to 7-membered carbon-based ring, optionally interrupted with at least one entity chosen from hetero atoms and groups bearing at least one hetero atom, such as oxygen and nitrogen; $R_1$ and $R_2$ possibly forming, together with the nitrogen atom to which they are attached, an optionally substituted 5- or 7-membered heterocycle optionally comprising another nitrogen or non-nitrogen hetero atom; the radicals $R_1$, $R_2$, and $R_3$ derived from $W'_6$, independently of each other, may optionally form, together with part of the group LK and with the nitrogen or oxygen atom to which each is attached, a saturated or unsaturated, aromatic or non-aromatic, optionally substituted 5- to 7-membered heterocycle;

$W_6$ is chosen from —$NR'_1$— and —O—, in which
$R'_1$ is chosen from hydrogen and a saturated or unsaturated, aromatic or non-aromatic, optionally substituted $C_1$–$C_{20}$ hydrocarbon-based chain, for example a $C_1$–$C_{16}$ hydrocarbon-based chain, which may form at least one optionally substituted 3- to 7-membered carbon-based ring, optionally interrupted with at least one entity chosen from hetero atoms and groups bearing at least one hetero atom, such as oxygen and nitrogen; and the radical $R'_1$ derived from $W_6$ may optionally form, together with the nitrogen atom to which it is attached and a part of the group LK, a saturated or unsaturated, aromatic or non-aromatic, optionally substituted 5- to 7-membered heterocycle optionally containing another hetero atom chosen from nitrogen and oxygen;

$W_2$, $W_5$ and $W'_5$, independently of each other, are chosen from formulae (a), (b), and (c) below:

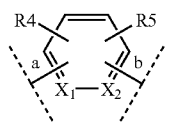

(a)

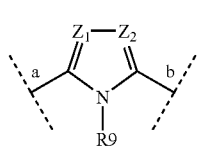

(b)

-continued

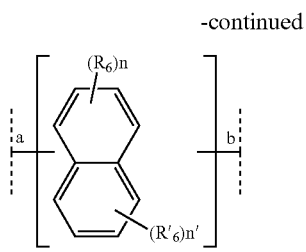
(c)

in which formulae:

X₁ is chosen from nitrogen and CR₇;
X₂ is chosen from nitrogen and CR₈;
Z₁ is chosen from nitrogen and CR₁₀;
Z₂ is chosen from nitrogen and CR₁₁;
R₄, R₅, R₆, R'₆, R₇, R₈, R₁₀ and R₁₁, independently of each other, are chosen from:
  linear or branched, saturated or unsaturated, aromatic or non-aromatic, optionally substituted $C_1$–$C_{16}$ hydrocarbon-based chains, which may form at least one optionally substituted 3- to 6-membered carbon-based ring, optionally interrupted with at least one entity chosen from hetero atoms and groups bearing at least one hetero atom, such as oxygen and nitrogen;
  hydroxyl groups,
  $C_1$–$C_4$ alkoxy groups; $C_2$–$C_4$ (poly)hydroxyalkoxy groups; alkoxycarbonyl groups (RO—CO—) in which R represents a $C_1$–$C_4$ alkyl radical; alkylcarbonyloxy radicals (RCO—O—) in which $R_a$ represents a $C_1$–$C_4$ alkyl radical;
  amino groups, amino groups substituted with at least one $C_1$–$C_4$ alkyl radical, which may be identical or different, optionally comprising at least one hydroxyl group, the two alkyl radicals possibly forming, together with the nitrogen atom to which they are attached, a 5- or 6-membered heterocycle optionally comprising another nitrogen or non-nitrogen hetero atom; alkylcarbonylamino groups ($R_b$CO—NR$_b$—) in which the radicals $R_b$, independently of each other, are chosen from $C_1$–$C_4$ alkyl radicals; carbamoyl groups (($R_c$)₂N—CO) in which the radicals $R_c$, independently of each other, are chosen from hydrogen and $C_1$–$C_4$ alkyl radicals; ureido groups (N($R_d$)₂—CO—NR'—) in which the radicals $R_d$ and R', independently of each other, are chosen from hydrogen and $C_1$–$C_4$ alkyl radicals; sulfonamide groups (($R_e$)₂N—SO₂—) in which the radicals $R_e$, independently of each other, are chosen from hydrogen and $C_1$–$C_4$ alkyl radicals; alkylsulfonylamino groups ($R_f$SO₂—NR$_a$'—) in which the radicals $R_f$ and $R_a$', independently of each other, are chosen from hydrogen and $C_1$–$C_4$ alkyl radicals; guanidinium groups (($R_b$')₂N—C(=NH₂⁺)—NR$_g$—) in which the radicals $R_g$ and $R_b$', independently of each other, are chosen from hydrogen and $C_1$–$C_4$ alkyl radicals;
  nitro groups; cyano groups; and halogen atoms, such as chlorine and fluorine.
R₄, R₅, R₇, R₈, R₁₀, and R₁₁ may represent hydrogen; or R₄, R₅, R₆, R'₆, R₇, R₈, R₁₀, and R₁₁, independently of each other, may optionally form, together with all or some of the groups W₁, W₆, and W'₆, a saturated or unsaturated, aromatic or non-aromatic, optionally substituted 5- to 7-membered heterocycle.

R₄, R₅, R₆, R'₆, R₇, R₈, R₁₀, and R₁₁ may also be chosen from the bond from W₂ to W₁, from W₅ to W₆, or from W'₅ to W'₆ or to the group LK.

a represents the bond from W₂, W₅, or W'₅ to the azo group —N═N—;

b represents the bond from W'₅ to W'₆ or to the group LK;

R₉ is chosen from:
  hydrogen; and
  linear or branched, saturated or unsaturated, aromatic or non-aromatic, optionally substituted $C_1$–$C_{16}$ hydrocarbon-based chains, which may form at least one optionally substituted 3- to 7-membered carbon-based ring;

n and n' represent integers, wherein n+n' is less than or equal to 6; W₃ and W₄, independently of each other, are chosen from cationic heteroaromatic radicals represented by formulae (1) to (11) below:

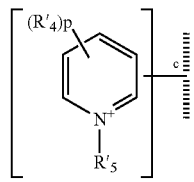
(1)

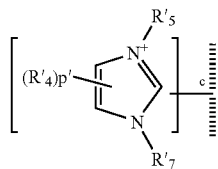
(2)

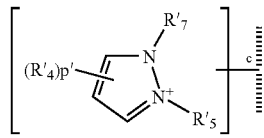
(3)

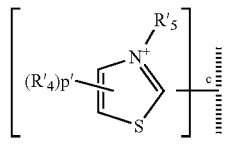
(4)

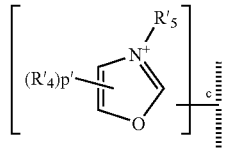
(5)

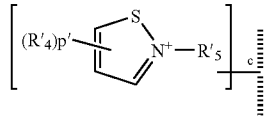
(6)

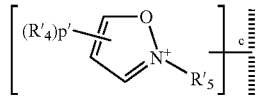
(7)

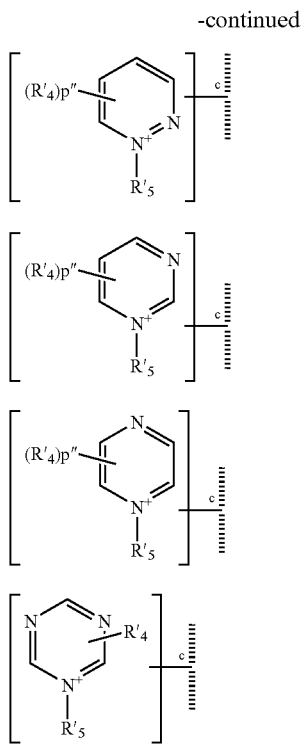

in which
R'$_4$, which may be identical or different, is chosen from:
  linear or branched, saturated or unsaturated, aromatic or non-aromatic, optionally substituted C$_1$–C$_{16}$ hydrocarbon-based chains, which may form at least one 3- to 6-membered carbon-based ring, optionally interrupted with at least one entity chosen from hetero atoms and groups comprising at least one hetero atom, such as oxygen and nitrogen;
  hydroxyl groups,
  C$_1$–C$_4$ alkoxy groups; C$_2$–C$_4$ (poly)hydroxyalkoxy groups; alkoxycarbonyl groups (R$_h$O—CO—) in which R$_h$ represents a C$_1$–C$_4$ alkyl radical; alkylcarbonyloxy radicals (R$_i$CO—O—) in which R$_i$ represents a C$_1$–C$_4$ alkyl radical;
  amino groups, amino groups substituted with at least one C$_1$–C$_4$ alkyl radical, independently of each other, optionally comprising at least one hydroxyl group, the two alkyl radicals possibly forming, together with the nitrogen atom to which they are attached, a 5- or 6-membered heterocycle optionally comprising another nitrogen or non-nitrogen hetero atom; alkylcarbonylamino groups (R$_j$CO—NR$_c$'—) in which the radical R$_j$ represents a C$_1$–C$_4$ alkyl radical and the radical R$_c$' is chosen from hydrogen and C$_1$–C$_4$ alkyl radicals; carbamoyl groups ((R$_k$)$_2$N—CO—) in which the radicals R$_k$, independently of each other, are chosen from hydrogen and C$_1$–C$_4$ alkyl radicals; ureido groups (N(R$_L$)$_2$—CO—NR$_d$'—) in which the radicals R$_L$ and R$_d$', independently of each other, are chosen from hydrogen and C$_1$–C$_4$ alkyl radicals; sulfonamide groups ((R$_m$)$_2$N—SO$_2$—) in which the radicals R$_m$, independently of each other, are chosen from hydrogen and C$_1$–C$_4$ alkyl radicals; alkylsulfonylamino groups (R$_n$SO$_2$—NR$_e$'—) in which the radicals R$_n$ and R$_e$', independently of each other, are chosen from hydrogen and C$_1$–C$_4$ alkyl radicals; guanidinium groups ((R$_f$')$_2$N—C(=NH$_2^+$)—NR$_p$—) in which the radicals R$_p$ and R$_f$', independently of each other, are chosen from hydrogen and C$_1$–C$_4$ alkyl radicals;
  nitro groups; cyano groups; and a halogen atoms, such as chlorine and fluorine;
two radicals R'$_4$ borne by two adjacent carbon atoms of the main ring may optionally form an aromatic or non-aromatic, 5- or 6-membered secondary ring, optionally substituted with at least one entity chosen from hydrogen; hydroxyl groups; C$_1$–C$_4$ alkyl radicals; C$_1$–C$_4$ alkoxy radicals; C$_2$–C$_4$(poly)hydroxyalkoxy radicals; amino radicals; and amino radicals substituted with at least one C$_1$–C$_4$ alkyl radical, which may be identical or different, optionally comprising at least one hydroxyl group; for example, the secondary ring may be a 6-membered aromatic ring optionally substituted as indicated above;
R'$_5$, borne by the quaternized nitrogen atom, in the case of W$_4$, is chosen from linear or branched, saturated or unsaturated, aromatic or non-aromatic, optionally substituted C$_1$–C$_{16}$ hydrocarbon-based chains, which may form at least one optionally substituted 3- to 6-membered carbon-based ring, optionally interrupted with at least one entity chosen from hetero atoms and groups comprising at least one hetero atom, such as oxygen and nitrogen; wherein the atom directly linking R'$_5$ to the quaternized nitrogen atom is a carbon atom; R'$_5$ borne by the quaternized nitrogen atom, in the case of W$_3$, represents a bond to LK;
R'$_7$ is chosen from optionally substituted C$_1$–C$_4$ alkyl radicals; optionally substituted phenyl radicals; and optionally substituted benzyl radicals;
the bond c links the cationic radical defined by formulae (1) to (11) to the azo group; wherein the bond may be on the main or secondary ring; and, in one embodiment, the bond c with the azo group is on the main ring;
p is an integer ranging from 0 to 4;
p' is an integer ranging from 0 to 2;
p'' is an integer ranging from 0 to 3; and
with the proviso that when the main ring does not bear the maximum number of substituents, then the unsubstituted position may bear a nitrogen atom;
LK is chosen from saturated or unsaturated, linear or branched, cyclic or non-cyclic, aromatic or non-aromatic, optionally substituted C$_2$–C$_{40}$ hydrocarbon-based chains, for example, C$_2$–C$_{20}$ hydrocarbon-based chains, bearing at least one cationic charge, optionally interrupted with at least one entity chosen from hetero atoms and groups comprising at least one hetero atom, such as oxygen and nitrogen; wherein
if LK is linked to W'$_5$, LK may end with at least one entity chosen from hetero atoms and groups comprising at least one hetero atom, such as oxygen and nitrogen;
if LK is linked to W'$_6$, LK may end with a group comprising at least one hetero atom chosen from —CO— and —SO$_2$—; and
if LK is linked to W$_3$, the bonding takes place via a carbon atom; and the electrical neutrality of the compounds may be ensured by at least one cosmetically acceptable anion An.
Also disclosed herein are dye compositions comprising, in a medium that is suitable for dyeing keratin fibers, at least one cationic diazo compound or the acid addition salt thereof, as a direct dye.

Further disclosed herein is a process for dyeing keratin fibers comprising placing the dye composition in contact with wet or dry fibers for a time that is sufficient to obtain the desired effect.

Finally, disclosed herein is a multi-compartment device comprising, in a first compartment, the composition according to the present disclosure, and, in a second compartment, at least one oxidizing composition.

It has been found that the compounds of formula (I) may show good fastness with respect to external agents such as shampoos, even when the keratin fiber is sensitized.

Furthermore, the compounds, which are dissymmetrical compounds may allow access to colorations that are less chromatic than those obtained with symmetrical compounds.

Other characteristics and advantages of the embodiments disclosed herein will emerge more clearly upon reading the description and examples that follow.

As used herein, unless otherwise indicated, the limits delimiting a range of values are included in that range.

Moreover, the keratin fibers forming the subject of the treatment disclosed herein are human keratin fibers, for example, human hair.

As used herein, and unless otherwise indicated:
an alkyl radical is linear or branched,
an alkyl radical or the alkyl part of a radical is said to be substituted when it comprises at least one substituent chosen from the following groups:
hydroxyl groups;
$C_1$–$C_4$ alkoxy groups; $C_2$–$C_4$ (poly)hydroxyalkoxy groups;
amino groups, and amino groups substituted with at least one $C_1$–$C_4$ alkyl group, which may be identical or different, optionally bearing at least one hydroxyl group, the alkyl group possibly forming, together with the nitrogen to which it is attached, a 5- or 6-membered heterocycle optionally comprising at least one other nitrogen or non-nitrogen hetero atom.

As used herein, an aryl or heteroaryl radical or the aryl or heteroaryl part of a radical is said to be substituted when it comprises at least one substituent borne by a carbon atom, which may be chosen from:
$C_1$–$C_{16}$ alkyl radicals, for example, $C_1$–$C_8$ alkyl radicals, optionally substituted with at least one radical chosen from hydroxyl radicals, $C_1$–$C_2$ alkoxy radicals, $C_2$–$C_4$ (poly)hydroxyalkoxy radicals, acylamino radicals, amino radicals substituted with two identical or different $C_1$–$C_4$ alkyl radicals, optionally bearing at least one hydroxyl group, or the two radicals possibly forming, together with the nitrogen atom to which they are attached, a 5- to 7-membered heterocycle, such as a 5- or 6-membered heterocycle, optionally comprising another nitrogen or non-nitrogen hetero atom;
halogen atoms such as chlorine, fluorine, and bromine;
hydroxyl groups;
$C_1$–$C_2$ alkoxy radicals; $C_2$–$C_4$ (poly)hydroxyalkoxy radicals;
amino radicals; amino radicals substituted with one or two identical or different $C_1$–$C_4$ alkyl radicals optionally bearing at least one hydroxyl group; and amino radicals with two optionally substituted $C_1$–$C_2$ alkyl radicals;
acylamino radicals (—$NR_q$—$COR_{g'}$) in which the radical $R_q$ is chosen from hydrogen; $C_1$–$C_4$ alkyl radicals optionally bearing at least one hydroxyl group, and the radical $R_{g'}$ is a $C_1$–$C_2$ alkyl radical; carbamoyl radicals ((R)$_2$N—CO—) in which the radicals R, which may be identical or different, are chosen from hydrogen and $C_1$–$C_4$ alkyl radicals optionally bearing at least one hydroxyl group; alkylsulfonylamino radicals (R'SO$_2$—NR—) in which the radical R is chosen from hydrogen and $C_1$–$C_4$ alkyl radicals optionally bearing at least one hydroxyl group, and the radical R' is chosen from $C_1$–$C_4$ alkyl radicals and phenyl radicals; and aminosulfonyl radicals ((R)$_2$N—SO$_2$—) in which the radicals R, which may be identical or different, are chosen from hydrogen and $C_1$–$C_4$ alkyl radicals optionally bearing at least one hydroxyl group, As used herein, the cyclic or heterocyclic part of a non-aromatic radical is said to be substituted when it comprises at least one substituent borne by a carbon atom, chosen from the following groups:
hydroxyl groups,
$C_1$–$C_4$ alkoxy groups, $C_2$–$C_4$ (poly)hydroxyalkoxy groups,
alkylcarbonylamino(($R_q$CO—$NR_{g'}$—) groups in which the radical $R_{g'}$ is chosen from hydrogen and $C_1$–$C_4$ alkyl radicals optionally bearing at least one hydroxyl group, and the radical $R_q$ is chosen from $C_1$–$C_2$ alkyl radicals and amino radicals substituted with two identical or different $C_1$–$C_4$ alkyl groups optionally comprising at least one hydroxyl group, the alkyl radicals possibly forming, together with the nitrogen atom to which they are attached, a 5- or 6-membered heterocycle optionally comprising at least one other nitrogen or non-nitrogen hetero atom.

As indicated above, in one embodiment disclosed herein, the composition may comprise compounds corresponding to the abovementioned formula (I).

In another embodiment, in the compound of formula (I), Dye1-LK-Dye2,
the radicals $R_1$, $R_2$, $R_3$, and $R'_1$, independently of each other, are chosen from
hydrogen;
optionally substituted $C_1$–$C_6$ alkyl radicals; and
aryl or arylalkyl radicals, such as phenyl and benzyl, the aryl radicals being optionally substituted;
the radicals $R_1$, $R_2$, and $R_3$, derived from $W'_6$, independently of each other, may optionally form, together with part of the group LK and with the nitrogen or oxygen atom to which each is attached, a saturated or unsaturated, aromatic or non-aromatic, optionally substituted 5- to 7-membered heterocycle; and the radical $R'_1$, derived from $W_6$, may optionally form, together with the nitrogen atom to which it is attached and part of the group LK, a saturated or unsaturated, aromatic or non-aromatic, optionally substituted 5-, 6-, or 7-membered heterocycle optionally containing another hetero atom chosen from nitrogen and oxygen.

In accordance with another embodiment of the present disclosure, the radicals $R_1$, $R_2$, $R_3$, and $R'_1$, which may be identical or different, are chosen from:
hydrogen;
optionally substituted $C_1$–$C_3$ alkyl radicals, such as methyl, ethyl, 2-hydroxyethyl, and 2-methoxyethyl radicals;
phenyl radicals, optionally substituted with at least one radical chosen from hydroxyl radicals, $C_1$–$C_2$ alkoxy radicals, amino radicals, and amino radicals substituted with at least one $C_1$–$C_4$ group optionally comprising at least one hydroxyl group;
radicals $R'_1$ derived from $W_6$ may form, together with the nitrogen atom to which they are attached and part of the group LK, a 5- or 6-membered heterocycle chosen from pyrrolidine, piperidine, piperazine, and homopiperazine heterocycles optionally substituted with at least one radical chosen from methyl, hydroxyl, amino, and (di)methylamino radicals.

According to a further embodiment of the present disclosure, the radicals $R_1$, $R_2$, $R_3$, and $R'_1$, which may be identical or different, are chosen from:

hydrogen;

methyl radicals; ethyl radicals; 2-hydroxyethyl radicals;

phenyl radicals, optionally substituted with at least one radical chosen from hydroxyl, methoxy, amino, (di) methylamino, and (di)(2-hydroxyethyl)amino radicals;

radicals $R'_1$ derived from $W_6$ may form, together with the nitrogen atom to which they are attached and part of the group LK, a 5- to 7-membered heterocycle such as pyrrolidine, 3-hydroxypyrrolidine, 3-dimethylaminopyrrolidine, piperidine, 2-(2-hydroxyethylpiperidine), 4-(aminomethyl)piperidine, 4-(2-hydroxyethyl) piperidine, 4-(dimethylamino)-piperidine, piperazine, 1-methylpiperazine, 1-(2-hydroxyethyl)piperazine, 1-(2-aminoethyl)piperazine, 1-hydroxyethylethoxypiperazine, homopiperazine, and 1-methyl-1,4-perhydrodiazepine.

Radicals $R_4$, $R_5$, $R_6$, $R'_6$, $R_7$, $R_8$, $R_{10}$, and $R_{11}$, which may be identical or different, may be chosen from:

optionally substituted $C_1$–$C_{16}$ alkyl radicals, for example, $C_1$–$C_8$ alkyl radicals;

halogen atoms such as chlorine, fluorine, and bromine;

hydroxyl groups;

$C_1$–$C_2$ alkoxy radicals; $C_2$–$C_4$ (poly)hydroxyalkoxy radicals;

amino radicals; amino radicals substituted with one or two $C_1$–$C_4$ alkyl radicals, which may be identical or different, optionally bearing at least one entity chosen from hydroxyl groups and $C_1$–$C_4$ dialkylamino groups;

alkylcarbonylamino radicals ($R_bO$—$NR_{b1}$-) in which the radical $R_b$ represents a $C_1$–$C_4$ alkyl radical and the radical $R_{b1}$ is chosen from hydrogen and $C_1$–$C_4$ alkyl radicals; carbamoyl radicals (($_{Rc}$)$_2$N—CO—) in which the radicals $R_c$, which may be identical or different, are chosen from hydrogen and $C_1$–$C_4$ alkyl radicals optionally comprising at least one hydroxyl group; alkylsulfonylamino radicals ($R_fSO_2$—$NR_a'$—) in which the radical $R_f$ is chosen from hydrogen and $C_1$–$C_4$ alkyl radicals optionally comprising at least one hydroxyl group, and the radical $R_a'$ represents a $C_1$–$C_4$ alkyl radical; aminosulfonyl radicals (($R_e$)$_2$N—$SO_2$—) in which the radicals $R_e$, which may be identical or different, are chosen from hydrogen and $C_1$–$C_4$ alkyl radicals optionally comprising at least one hydroxyl group; and bonds from $W'_5$ to $W'_6$.

Radicals $R_4$, $R_5$, $R_7$, $R_8$, $R_{10}$, and $R_{11}$ may also represent hydrogen.

In another embodiment, radicals $R_4$, $R_5$, $R_6$, $R'_6$, $R_7$, $R_8$, $R_{10}$ and $R_{11}$, which may be identical or different, are chosen from:

$C_1$–$C_4$ alkyl radicals optionally substituted with at least one radical chosen from hydroxyl radicals, acylamino radicals, amino radicals substituted with two identical or different $C_1$–$C_2$ alkyl radicals, optionally comprising at least one hydroxyl group, and $C_1$–$C_2$ alkoxy radicals;

amino radicals; amino radicals substituted with one or two identical or different. $C_1$–$C_2$ alkyl radicals, optionally comprising at least one hydroxyl group; acylamino radicals; carbamoyl radicals; sulfonylamino radicals; hydroxyl radicals; $C_1$–$C_2$ alkoxy radicals; and bonds from $W'_5$ to $W'_6$.

Radicals $R_4$, $R_5$, $R_7$, $R_8$, $R_{10}$ and $R_{11}$ may also represent hydrogen.

In a further embodiment of the present disclosure, radicals $R_4$, $R_5$, $R_6$, $R'_6$, $R_7$, $R_8$, $R_{10}$, and $R_{11}$, independently of each other, are chosen from:

methyl radicals, ethyl radicals, propyl radicals, 2-hydroxyethyl radicals, methoxy radicals, ethoxy radicals, 2-hydroxyethyloxy radicals, 3-hydroxy-propyloxy radicals, 2-methoxyethyl radicals;

sulfonylamino radicals; amino radicals, methylamino radicals, dimethylamino radicals, 2-hydroxyethylamino radicals, 3-hydroxypropylamino radicals, acylamino radicals, hydroxyl radicals;

chlorine; and bonds from $W'_5$ to $W'_6$.

Radicals $R_4$, $R_5$, $R_7$, $R_8$, $R_{10}$, and $R_{11}$ may also represent hydrogen.

In one embodiment, radical $R_9$ is chosen from hydrogen; $C_1$–$C_{15}$ alkyl radicals; $C_2$–$C_6$ monohydroxyalkyl radicals; $C_2$–$C_6$-polyhydroxyalkyl radicals; ($C_1$–$C_6$)alkoxy($C_2$–$C_6$) alkyl radicals; optionally substituted aryl radicals, such as phenyl radicals; optionally substituted arylalkyl radicals, such as benzyl radicals; $C_2$–$C_6$ amidoalkyl radicals; $C_2$–$C_6$ aminoalkyl radicals, the amine of which may be substituted with two identical or different, optionally substituted $C_1$–$C_4$ alkyl radicals.

In another embodiment, $R_9$ is chosen from hydrogen; $C_1$–$C_6$ alkyl radicals; $C_2$–$C_6$ monohydroxyalkyl radicals; $C_2$–$C_6$ polyhydroxyalkyl radicals; ($C_1$–$C_6$)alkoxy($C_2$–$C_6$) alkyl radicals; phenyl radicals optionally substituted with at least one chlorine atom, hydroxyl groups, groups RCO—NH— in which R is chosen from $C_1$–$C_4$ alkyl radicals or amino radicals substituted with two identical or different $C_1$–$C_4$ alkyl radicals; benzyl radicals; $C_1$–$C_6$ aminoalkyl radicals; $C_1$–$C_6$ aminoalkyl radicals in which the amine may be substituted with two identical or different $C_1$–$C_4$ alkyl radicals.

According to one embodiment, $W_2$, $W_5$, and $W'_5$, independently of each other, are chosen from formulae (a) and (c). According to this embodiment, $X_1$ may represent $CR_7$ and $X_2$ may represent $CR_8$. Further, in accordance with this embodiment, $R_4$, $R_5$, $R_6$, $R'_6$, $R_7$, and $R_8$, independently of each other, may have the same meanings as above. In another embodiment, groups $W_3$ and $W_4$, independently of each other, may be chosen from heterocycles of formulae (1), (2), and (3) below:

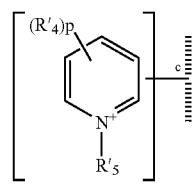

(1)

-continued

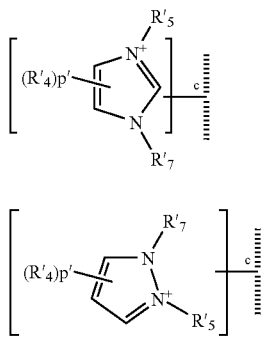

(2)

(3)

in which $R'_4$, $R'_5$, $R'_7$, p, p', and a are defined as above. In one embodiment, $R'_5$, when derived from $W_4$, and $R'_7$ may have the same definitions as $R_9$, except that $R'_5$ and $R'_7$ may not represent hydrogen.

In accordance with one embodiment disclosed herein, the cationic aromatic heterocyclic groups $W_3$ and $W_4$, independently of each other, are chosen from 2-imidazolium, 2-benzimidazolium, 2-pyridinium, 3-pyridinium, 4-pyridinium, 2-quinolinium, 4-quinolinium, 3-pyrazolium, 4-pyrazolium, 3-indazolium, 4-indazolium, 5-indazolium, 6-indazolium, and 7-indazolium.

According to another embodiment disclosed herein, the groups $W_3$ and $W_4$, independently of each other, are chosen from cationic aromatic heterocycles chosen from 2-imidazolium, 2-pyridinium, 3-pyridinium, 4-pyridinium, 2-quinolinium, 4-quinolinium, 3-pyrazolium, 4-pyrazolium, 3-indazolium, 4-indazolium, and 7-indazolium. In the case of $W_3$, the cationic heterocyclic radicals may be attached to the group LK via a quaternized nitrogen atom, for example, via radical $R'_5$.

In accordance with a further embodiment, LK may be represented by the following formula:

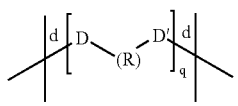

in which
D and D', independently of each other, are chosen from linear or branched, saturated or unsaturated $C_1$–$C_{14}$ hydrocarbon-based bonds, optionally interrupted with at least one entity chosen from hetero atoms and groups comprising at least one hetero atom, such as oxygen and nitrogen;
the bond d links the arms D and D' to the groups $W_3$, $W_6$, and $W'_5$;
q is greater than or equal to 1, for example, q is equal to 1 or 2;
R is chosen from the formulae (d), (e), and (f):

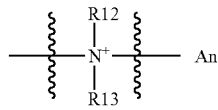

(d)

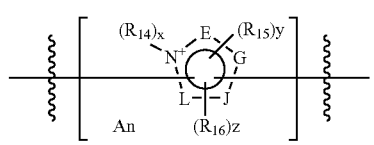

(e)

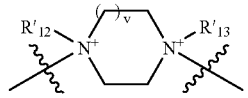

(f)

wherein $R_{12}$, $R_{13}$, $R'_{12}$, and $R'_{13}$, independently of each other, are chosen from $C_1$–$C_{15}$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals, such as phenyl radicals;
arylalkyl radicals, such as benzyl radicals; $C_1$–$C_6$ amidoalkyl radicals; $C_1$–$C_6$ aminoalkyl radicals; $C_1$–$C_6$ aminoalkyl radicals in which the amine may be substituted with at least one identical or different $C_1$–$C_4$ alkyl group; ($C_1$–$C_6$)alkylcarbonyl radicals; acylamino radicals; and ($C_1$–$C_6$)alkylsulfonyl radicals;
$R_{12}$ and $R_{13}$ may form, together with the nitrogen atom to which they are attached, a 5-, 6-, or 7-membered saturated cationic ring that may contain at least one hetero atom, the cationic ring possibly being substituted with at least one halogen atom; hydroxyl radicals; $C_1$–$C_6$ alkyl radicals; $C_1$–$C_6$ monohydroxyalkyl radicals; $C_2$–$C_6$ polyhydroxyalkyl radicals; $C_1$–$C_6$ alkoxy radicals;
amido radicals; ($C_1$–$C_6$)alkylcarbonyl radicals; thio radicals; $C_1$–$C_6$ thioalkyl radicals; ($C_1$–$C_6$)alkylthio radicals; amino radicals; and amino radicals optionally substituted with at least one radical chosen from $C_1$–$C_6$ alkyl radicals, ($C_1$–$C_6$)alkylcarbonyl radicals, acylamino radicals, and ($C_1$–$C_6$)alkylsulfonyl radicals;
$R_{12}$ or $R_{13}$ may form, together with D or D', a 5-, 6-, or 7-membered saturated cationic ring that may contain at least one hetero atom, the cationic ring possibly being substituted with an entity chosen from halogen atoms; hydroxyl radicals; $C_1$–$C_6$ alkyl radicals; $C_1$–$C_6$ monohydroxyalkyl radicals; $C_2$–$C_6$ polyhydroxyalkyl radicals; $C_1$–$C_6$ alkoxy radicals; amido radicals; ($C_1$–$C_6$) alkylcarbonyl radicals; thio radicals; $C_1$–$C_6$ thioalkyl radicals; ($C_1$–$C_6$)alkylthio radicals; amino radicals; and amino radicals optionally substituted with at least one radical chosen from $C_1$–$C_6$ alkyl radicals, ($C_1$–$C_6$) alkylcarbonyl radicals, acylamino radicals, and ($C_1$–$C_6$)alkylsulfonyl radicals;
$R_{12}$ and $R_{13}$ may form, together with $W_1$ or $W_6$, a 5-, 6-, or 7-membered, saturated or unsaturated, aromatic or non-aromatic, optionally substituted cationic heterocycle;
the ring members E, G, J, and L, which may be identical or different, are chosen from carbon, oxygen, sulfur, and nitrogen such that they may form a ring chosen from pyrazolium, imidazolium, triazolium, oxazolium, isoxazolium, thiazolium, and isothiazolium rings, $R_{14}$ may have the same meaning as $R_{12}$, independently of $R_{12}$;

$R_{15}$ is chosen from $C_1$–$C_6$ alkyl radicals; $C_1$–$C_6$ monohydroxyalkyl radicals, $C_2$–$C_6$ polyhydroxyalkyl radicals, ($C_1$–$C_6$)alkoxy($C_1$–$C_6$)alkyl radicals, $C_2$–$C_6$ carbamylalkyl radicals, ($C_1$–$C_6$)alkylcarboxy($C_1$–$C_6$) alkyl radicals, and benzyl radicals; wherein the radical $R_{15}$ may be borne by a nitrogen atom;

$R_{16}$, which may be identical or different, is chosen from hydrogen; halogen atoms; $C_1$–$C_6$ alkyl radicals; $C_1$–$C_6$ monohydroxyalkyl radicals; $C_2$–$C_6$ polyhydroxyalkyl radicals; $C_1$–$C_6$ alkoxy radicals; amido radicals; carboxyl radicals; $C_1$–$C_6$ alkylcarbonyl radicals; $C_1$–$C_6$ thioalkyl radicals; ($C_1$–$C_6$)alkylthio radicals; amino radicals disubstituted with at least one radical chosen from ($C_1$–$C_6$)alkyl radicals, ($C_1$–$C_6$)alkylcarbonyl radicals, and ($C_1$–$C_6$)alkylsulfonyl radicals; benzyl radicals;

phenyl radicals optionally substituted with at least one radical chosen from methyl, hydroxyl, amino, and methoxy radicals; wherein radicals $R_{16}$ is borne by a carbon atom;

An represents an anion chosen from organic and mineral anions;

z is an integer ranging from 1 to 3;

y is equal to 0 or 1;

v is an integer equal to 1 or 2; and x is equal to 0 or 1; wherein
when x is 0, one of the linker arms D or D' is attached to the quaternized nitrogen atom; and when x is 1, at least one of the linker arms D and/or D' is attached to a carbon atom.

According to one embodiment of formula (d), $R_{12}$ and $R_{13}$, separately, may be chosen from $C_1$–$C_6$ alkyl radicals, $C_1$–$C_4$ monohydroxyalkyl radicals, $C_2$–$C_4$ polyhydroxyalkyl radicals, ($C_1$–$C_6$)alkoxy($C_2$–$C_4$)alkyl radicals, $C_2$–$C_6$ amidoalkyl radicals, and $C_2$–$C_6$ dimethylaminoalkyl radicals. In another embodiment, $R_{12}$ and $R_{13}$, may be separately chosen from methyl radicals, ethyl radicals, and 2-hydroxyethyl radicals.

According to this embodiment, D and D', may be separately chosen from substituted and unsubstituted $C_1$–$C_6$ alkyl chains. For example, D and D' may be chosen from unsubstituted $C_1$–$C_6$ alkyl chains.

According to one embodiment of formula (e), the ring members E, G, J, and L may form a ring chosen from imidazolium, pyrazolium, oxazolium, and thiazolium rings. According to this embodiment, x and b are equal to 0. Further, in accordance with this embodiment, D and D' are chosen from substituted and unsubstituted $C_1$–$C_4$ alkyl chains. Moreover, $R_{14}$ may be chosen from methyl radicals, ethyl radicals, and 2-hydroxyethyl radicals.

According to one embodiment of formula (f), $R'_{12}$ and $R'_{13}$ may have the same meanings as $R_{12}$ and $R_{13}$, independently of these two radicals. According to this embodiment, D and D', may separately represent a substituted or unsubstituted $C_1$–$C_6$ alkyl chain. Further, in this embodiment, the coefficient v may be equal to 1.

The anion An is chosen from organic anions, mineral anions, and mixture of anions, which may be chosen so as to respect the electrical neutrality of the compound, for example, the anion may be chosen from halides, such as chlorides, bromides, fluorides, and iodides; hydroxides; sulfates; hydrogen sulfates; ($C_1$–$C_6$)alkyl sulfates, for instance methyl sulfate and ethyl sulfate; phosphates; carbonates; hydrogen carbonates; perchlorates; acetates; tartrates; citrates; oxalates; and ($C_1$–$C_6$)alkylsulfonates, such as methylsulfonate; arylsulfonates, which may be unsubstituted or substituted with a $C_1$–$C_4$ alkyl radical, for instance, a 4-tolylsulfonate.

The acid addition salts of the compounds of formula (I) may be, for example, be chosen from halides, for instance chlorides and bromides; sulfates; linear or branched $C_1$–$C_6$ alkyl sulfates, for instance methosulfate and ethosulfate ions; hydrogen carbonates; perchlorates; and carboxylic acid salts, for instance, at least one of acetates, citrates; and tartrates.

Non-limiting examples of compounds in accordance with one embodiment include compounds chosen from the following formulae:

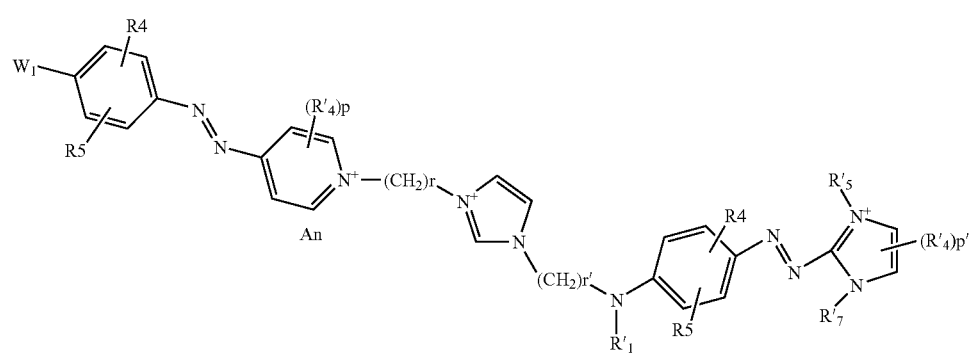

-continued
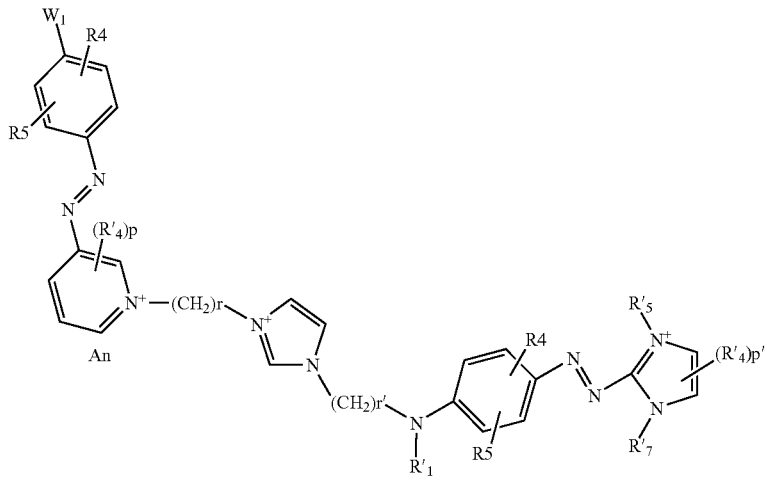
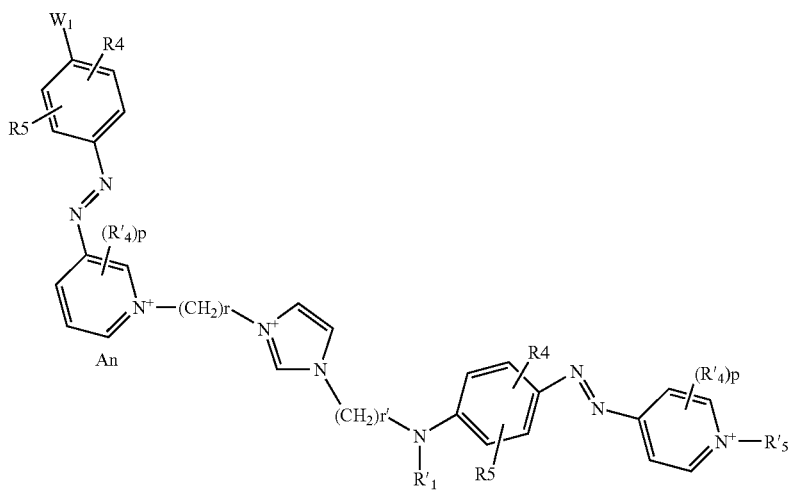
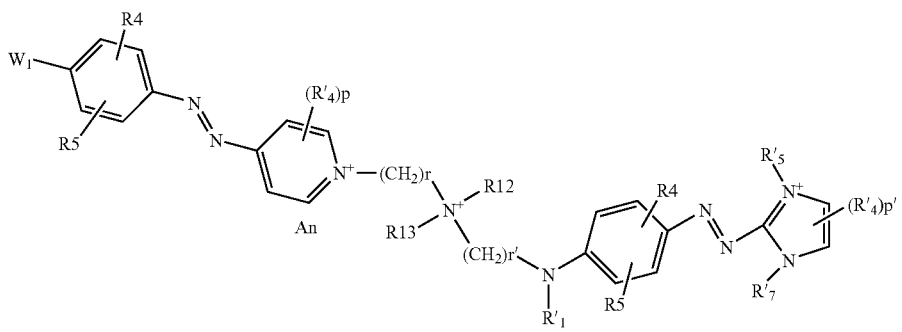

-continued

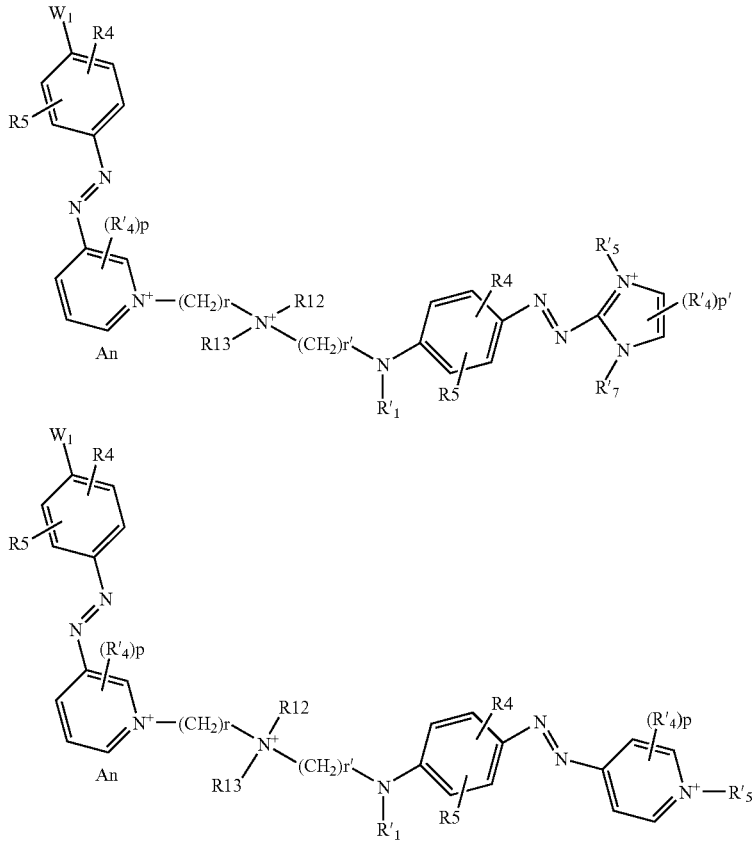

in which formulae $W_1$, $R_4$, $R_5$, $R'_1$, $R'_4$, $R_{12}$, $R_{13}$, $R'_5$, $R'_7$, p, and p' are as defined above;

r and r', which may be identical or different, are chosen from integers ranging from 1 to 10, for example, integers ranging from 1 to 6; and the electrical neutrality of the molecule may be respected by the presence of at least one cosmetically acceptable anion An as defined above.

These compounds may be obtained from preparation processes described, for example, in U.S. Pat. No. 5,708,151; J. Chem. Res., Synop. (1998), (10), 648–649; U.S. Pat. Nos. 3,151,106 and 5,852,179; Heterocycles, 1987, 26 (2) 313–317; Synth. Commun. 1999, 29 (13), 2271–2276; and Tetrahedron, 1983, 39 (7), 1091–1101.

Also herein disclosed is a composition comprising, in a medium that is suitable for dyeing keratin fibers, at least one compound of formula (I), or an acid addition salt thereof, as direct dye.

The concentration of the compound of formula (I) or, if more than one compound of formula (I) is used, the total concentration of the compounds of formula (I) may range from 0.001% to 20% by weight, for example, from 0.01% to 10% by weight or from 0.05% by 5% by weight, relative to the total weight of the dye composition.

The composition disclosed herein may also comprise at least one oxidation base. This at least one oxidation base may be chosen from the oxidation bases conventionally used in oxidation dyeing, for example, para-phenylenediamines, bis(phenyl)alkylenediamines, para-aminophenols, ortho-aminophenols, and heterocyclic bases.

Non-limiting examples of para-phenylenediamines include, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the acid addition salts thereof.

In one embodiment, the para-phenylenediamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-paraphenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

Examples of bis(phenyl)alkylenediamines include, but are not limited to, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis-(ethyl)-N,N'-bis(4'-amino-3'-methylphenyl)ethylenediamine and 1,8-bis(2,5-diaminophenoxy)-3,6-dioxaoctane, and the acid addition salts thereof.

Non-limiting examples of suitable para-aminophenols may include, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Examples of ortho-aminophenols include, but are not limited to, 2-aminophenol, 2-amino-5-methylphenol, 2-amino-6-methylphenol, 5-acetamido-2-aminophenol, and the acid addition salts thereof.

Suitable heterocyclic bases may be chosen from, for example, pyridine derivatives, pyrimidine derivatives, and pyrazole derivatives.

Non-limiting examples of pyridine derivatives include, for example, the compounds described in British Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the acid addition salts thereof.

Examples of pyrimidine derivatives include, but are not limited to, the compounds described, for example, in the patent documents DE 2 359 399; JP 88-169 571; JP 05-163 124; EP 0 770 375; and patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, and 2,5,6-triaminopyrimidine; and pyrazolopyrimidine derivatives such as those mentioned in French Patent Application No. FR-A-2 750 048, for example, pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine; the acid addition salts thereof; and the tautomeric forms thereof, when a tautomeric equilibrium exists.

Suitable pyrazole derivatives may be chosen from, for example, the compounds described in German Patent Nos. DE 3 843 892 and DE 4 133 957 and patent applications WO 94/08969, WO 94/08970, FR-A-2 733 749, and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the acid addition salts thereof.

The composition according to one embodiment may also comprise at least one coupler conventionally used for dyeing keratin fibers. Such couplers, include, but are not limited to, meta-phenylenediamines, meta-aminophenols, meta-diphenols, naphthalene-based couplers, and heterocyclic couplers.

Further examples of suitable couplers include, but are not limited to 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxy-pyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxy-ethylamino)toluene, and the acid addition salts thereof.

In the composition according to one aspect of the present disclosure, the at least one coupler may be present in an amount ranging from 0.001% to 10% by weight, for example from 0.005% to 6% by weight, relative to the total weight of the dye composition. The at least one oxidation base may be present in an amount ranging from 0.001% to 10% by weight, for example, from 0.005% to 6% by weight, relative to the total weight of the dye composition.

In certain embodiments, the acid addition salts that may be used for the at least one oxidation base and/or at least one coupler in the context of the dye compositions disclosed herein may be chosen from hydrochlorides, hydrobromides, sulfates, citrates, succinates, tartrates, lactates, tosylates, benzenesulfonates, phosphates, and acetates.

The composition according to one embodiment may optionally comprise at least one additional direct dye other than the compounds of formula (I). This at least one additional direct dye may be chosen from cationic and nonionic species.

Non-limiting examples of additional direct dyes include at least one of nitrobenzene dyes, azo dyes, azomethine dyes, methane dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylmethane-based dyes, and natural dyes.

The at least one additional direct dye may be chosen, for example, from the following red or orange nitrobenzene dyes:

1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The at least one additional direct dye may also be chosen from yellow and green-yellow nitrobenzene direct dyes; for example:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Blue or violet nitrobenzene direct dyes may also be used, for instance:
1-(β-hydroxyethyl)amino-4-N,N-bis(β-hydroxyethyl)amino-2-nitrobenzene,
1-(γ-hydroxypropyl)amino-4,N,N-bis(β-hydroxyethyl amino-2-nitrobenzene
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines having the following formula:

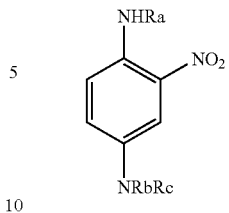

in which:
R$_b$ is chosen from C$_1$–C$_4$ alkyl radicals, β-hydroxyethyl radicals, β-hydroxypropyl radicals, and γ-hydroxypropyl radicals;
R$_a$ and R$_c$, which may be identical or different, are chosen from β-hydroxyethyl radicals, β-hydroxypropyl radicals, γ-hydroxypropyl radicals, and β,γ-dihydroxypropyl radicals, with the proviso that
at least one of the radicals R$_b$, R$_c$ or R$_a$ represents a γ-hydroxypropyl radical; and
R$_b$ and R$_c$ do not simultaneously denote a β-hydroxyethyl radical when R$_b$ is γ-hydroxypropyl radical, such as those described in French Patent No. FR 2 692 572.

Among the non-limiting examples of azo direct dyes that may be used according to the present disclosure, include cationic azo dyes described in patent applications WO 95/15144, WO 95/01772, and EP 714 954, for example, 1,3-dimethyl-2-[[4-(dimethylamino)phenyl]azo]-1H-imidazolium chloride, 1,3-dimethyl-2-[(4-aminophenyl)azo]-1H-imidazolium chloride, and 1-methyl-4-[(methylphenylhydrazono)methyl]pyridinium methyl sulfate.

Among these compounds, mention may be made of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methyl sulfate.

Among the azo direct dyes that may also be mentioned are the following dyes described in the Colour Index International 3rd edition:
Disperse Red 17,
Acid Yellow 9,
Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23,
Acid Orange 24, and
Disperse Black 9.

Further non-limiting examples of azo direct dyes include 1-(4'-aminodiphenylazo)-2-methyl-4-[bis(β-hydroxyethyl)amino]benzene, and 4-hydroxy-3-(2-methoxyphenylazo)-1-naphthalenesulfonic acid.

Examples of suitable quinone direct dyes include, but are not limited to, the following dyes:
Disperse Red 15, Solvent Violet 13,
Acid Violet 43,
Disperse Violet 1,
Disperse Violet 4,
Disperse Blue 1,
Disperse Violet 8,
Disperse Blue 3,
Disperse Red 11,
Acid Blue 62,
Disperse Blue 7,
Basic Blue 22,
Disperse Violet 15,
Basic Blue 99,
and the following compounds:
1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone, and
1,4-bis(β,γ-dihydroxypropylamino)anthraquinone.

Suitable azine dyes may be chosen from, for example, Basic Blue 17 and Basic Red 2.

Non-limiting examples of triarylmethane dyes may include the following compounds:
Basic Green 1,
Acid Blue 9,
Basic Violet 3,
Basic Violet 14,
Basic Blue 7,
Acid Violet 49,
Basic Blue 26, and
Acid Blue 7.

Examples of suitable indoamine dyes include, but are not limited to, the following compounds:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N (3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

Suitable tetraazapentamethine type dyes may be chosen from, for example, the compounds given in the table below, where An is defined as above:

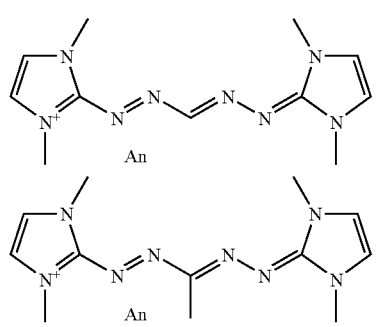

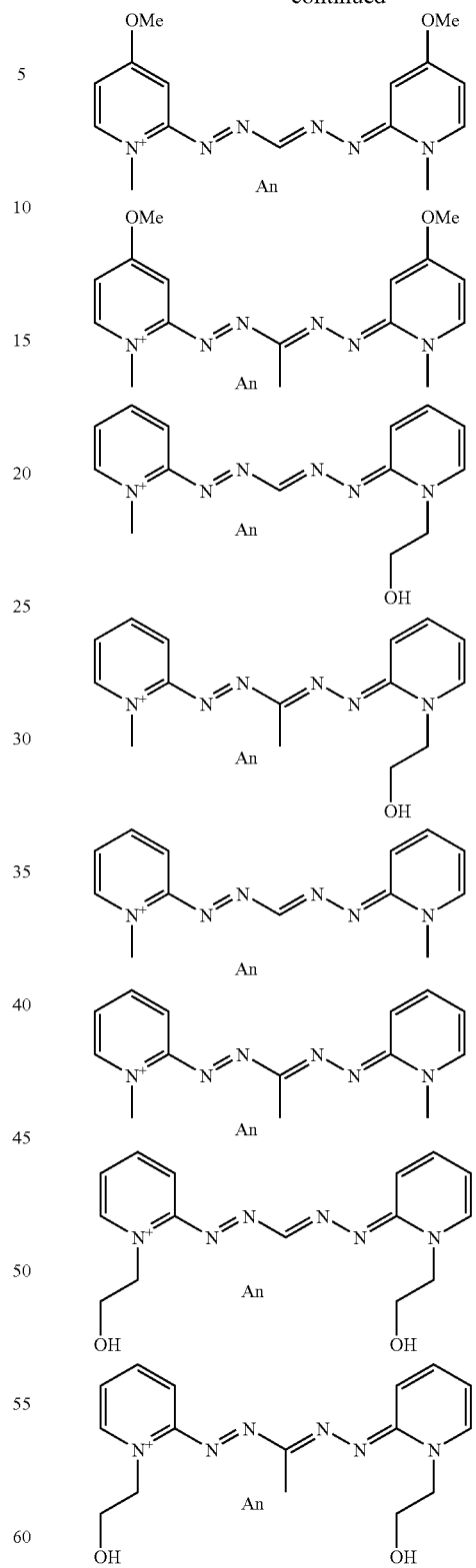

Non-limiting examples of natural direct dyes include lawsone, juglone, alizarin, purpurin, carminic acid, kermesic acid, purpurogallin, protocatechaldehyde, indigo, isatin, curcumin, spinulosin, and apigenidin. Extracts or decoctions containing these natural dyes may also be used, for example, henna-based poultices and extracts.

When present, the content of the at least one additional direct dye in the composition may range from 0.001% to 20% by weight, for example, from 0.01% to 10% by weight, relative to the total weight of the composition.

A medium that is suitable for dyeing, also known as the dye support, may be used in a composition in accordance with one embodiment of the present disclosure and may comprise water or of a mixture of water and at least one organic solvent to dissolve the compounds that may not be sufficiently water-soluble.

The at least one organic solvent may be chosen from linear or branched, saturated and unsaturated monoalcohols or diols containing from 2 to 10 carbon atoms, such as ethyl alcohol, isopropyl alcohol, hexylene glycol (2-methyl-2,4-pentanediol), neopentyl glycol, and 3-methyl-1,5-pentanediol; aromatic alcohols such as benzyl alcohol and phenylethyl alcohol; glycols and glycol ethers, for instance, ethylene glycol monomethyl, monoethyl, and monobutyl ether; propylene glycol and its ethers, for instance propylene glycol monomethyl ether, butylene glycol, and dipropylene glycol; and diethylene glycol alkyl ethers, for example, $C_1$–$C_4$ alkyl ethers, such as diethylene glycol monoethyl ether, and monobutyl ether.

The solvents described above, when present, may be present in an amount ranging from 1% to 40% by weight, for example, from 5% to 30% by weight, relative to the total weight of the composition.

The dye composition in accordance with one embodiment of the present disclosure may also comprise various adjuvants conventionally used in compositions for dyeing the hair, such as at least one of anionic, cationic, nonionic, amphoteric or zwitterionic surfactants; anionic, cationic, nonionic, amphoteric or zwitterionic polymers; mineral and organic thickeners, such as anionic, cationic, non-ionic, and amphoteric associative polymeric thickeners; antioxidants; penetrating agents; sequestering agents; fragrances; buffers; dispersants; conditioning agents, for instance, silicones, which may or may not be volatile or modified; film-forming agents; ceramides; preserving agents; and opacifiers.

The above adjuvants, when present, may each be present in an amount ranging from 0.01% to 20% by weight, relative to the total weight of the composition.

Needless to say, a person skilled in the art will take care to select this or these optional additional compounds such that the advantageous properties intrinsically associated with the oxidation dye composition in accordance with the present disclosure are not, or are not substantially, adversely affected by the envisaged addition(s). The pH of the dye composition in accordance with one embodiment disclosed herein may range from 3 to 12, for example, from 5 to 11. It may be adjusted to the desired value using acidifying or basifying agents conventionally used in the dyeing of keratin fibers, or alternatively, using standard buffer systems.

Suitable acidifying agents may be chosen from, for example, mineral or organic acids such as hydrochloric acid, orthophosphoric acid, and sulfuric acid; carboxylic acids such as acetic acid, tartaric acid, citric acid, and lactic acid; and sulfonic acids.

Examples of basifying agents that may be mentioned are aqueous ammonia; alkaline carbonates; alkanolamines such as monoethanolamine, diethanolamine, triethanolamine, and derivatives thereof; sodium hydroxide; potassium hydroxide; and compounds having the following formula:

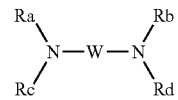

in which W represents a propylene residue optionally substituted with a radical chosen from hydroxyl groups and $C_1$–$C_4$ alkyl radicals; and $R_a$, $R_b$, $R_c$, and $R_d$, which may be identical or different, are chosen from hydrogen, $C_1$–$C_4$ alkyl radicals, and $C_1$–$C_4$ hydroxyalkyl radicals.

The dye composition disclosed herein may be in various forms, such as in the form of liquids, creams, gels, and any other form that is suitable for dyeing keratin fibers, such as human hair.

The composition disclosed herein may also comprise at least one oxidizing agent. In this case, the composition may be referred to as a ready-to-use composition.

As used herein, the term "ready-to-use composition" means a composition intended to be applied immediately to the keratin fibers, i.e. it may be stored in unmodified form before use or may result from the extemporaneous mixing of two or more compositions.

The composition may also be obtained by mixing the composition according to the invention with an oxidizing composition.

The at least one oxidizing agent may be any oxidizing agent conventionally used in the field, for example, hydrogen peroxide; urea peroxide; alkali metal bromates; persalts such as perborates and persulfates; and enzymes, such as peroxidases, 2-electron oxidoreductases such as uricases, and 4-electron oxygenases such as laccases. In one embodiment, the oxidizing agent is hydrogen peroxide.

The content of oxidizing agent may range from 1% to 40% by weight, for example, from 1% to 20% by weight, relative to the total weight of the ready-to-use composition.

In certain embodiments, the oxidizing composition used is an aqueous composition and may be in the form of a solution or an emulsion.

In certain embodiments, to obtain a ready-to-use composition, the composition free of oxidizing agent is mixed with about 0.5 to 10 weight equivalents of the oxidizing composition.

In one embodiment disclosed herein, the pH of the ready-to-use composition ranges from 4 to 12, for example, from 7 to 11.5.

The pH of the composition may be adjusted using an acidifying or basifying agent chosen for example from those mentioned above.

Further herein disclosed is a dyeing process comprising applying a dye composition as disclosed herein to wet or dry keratin fibers.

The application to the fibers of the dye composition comprising at least one compound of formula (I) or the acid addition salts thereof, optionally at least one oxidation base optionally combined with at least one coupler, and optionally at least one additional direct dye, may be performed in the presence of at least one oxidizing agent.

This at least one oxidizing agent may be added to the composition comprising the at least one compound of formula (I) and the optional oxidation bases, couplers, and/or additional direct dyes, either at the time of use or directly onto the keratin fiber.

The oxidizing composition may also comprise various adjuvants conventionally used in compositions for dyeing the hair and as defined above.

The pH of the oxidizing composition containing the at least one oxidizing agent is such that, after mixing with the dye composition, the pH of the resulting composition applied to the keratin fibers may range from 4 to 12, for example, from 7 to 11.5. The pH may be adjusted to the desired value by using acidifying or basifying agents as defined above.

The composition that is applied to the keratin fibers may be in various forms, such as in the form of liquids, creams, gels, and any other form that is suitable for dyeing keratin fibers, such as human hair.

According to one embodiment, the dye composition may be substantially free of oxidation bases and couplers.

The composition applied may optionally comprise at least one oxidizing agent.

The composition is thus applied to the wet or dry keratin fibers and is then left for a leave-in time that is sufficient to obtain the desired coloration.

Regardless of whether the dye composition does or does not comprise an oxidizing agent, the leave-in time may range from a few seconds to one hour, for example, from 3 to 30 minutes.

The temperature at which the composition is left to act may range from 15 to 220° C., such as from 15 to 80° C. or from 15 to 40° C.

After the leave-in time, the composition may be removed by rinsing with water, optionally followed by washing with shampoo, and then optionally drying.

Also described herein is a multi-compartment device or dyeing "kit" in which a first compartment comprises the dye composition disclosed herein and a second compartment comprises the at least one oxidizing composition. This device may be equipped with a means for applying the desired mixture to the hair, such as the devices described in French Patent No. FR 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

The examples that follow serve to illustrate certain embodiments of the disclosure without, however, being limiting in nature.

EXAMPLES

Example 1

Synthesis of the Compound Below

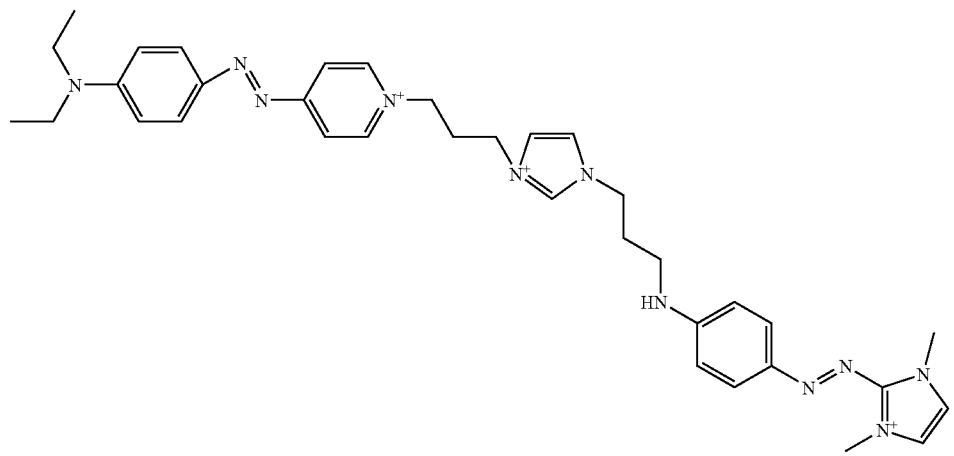

Synthetic Scheme

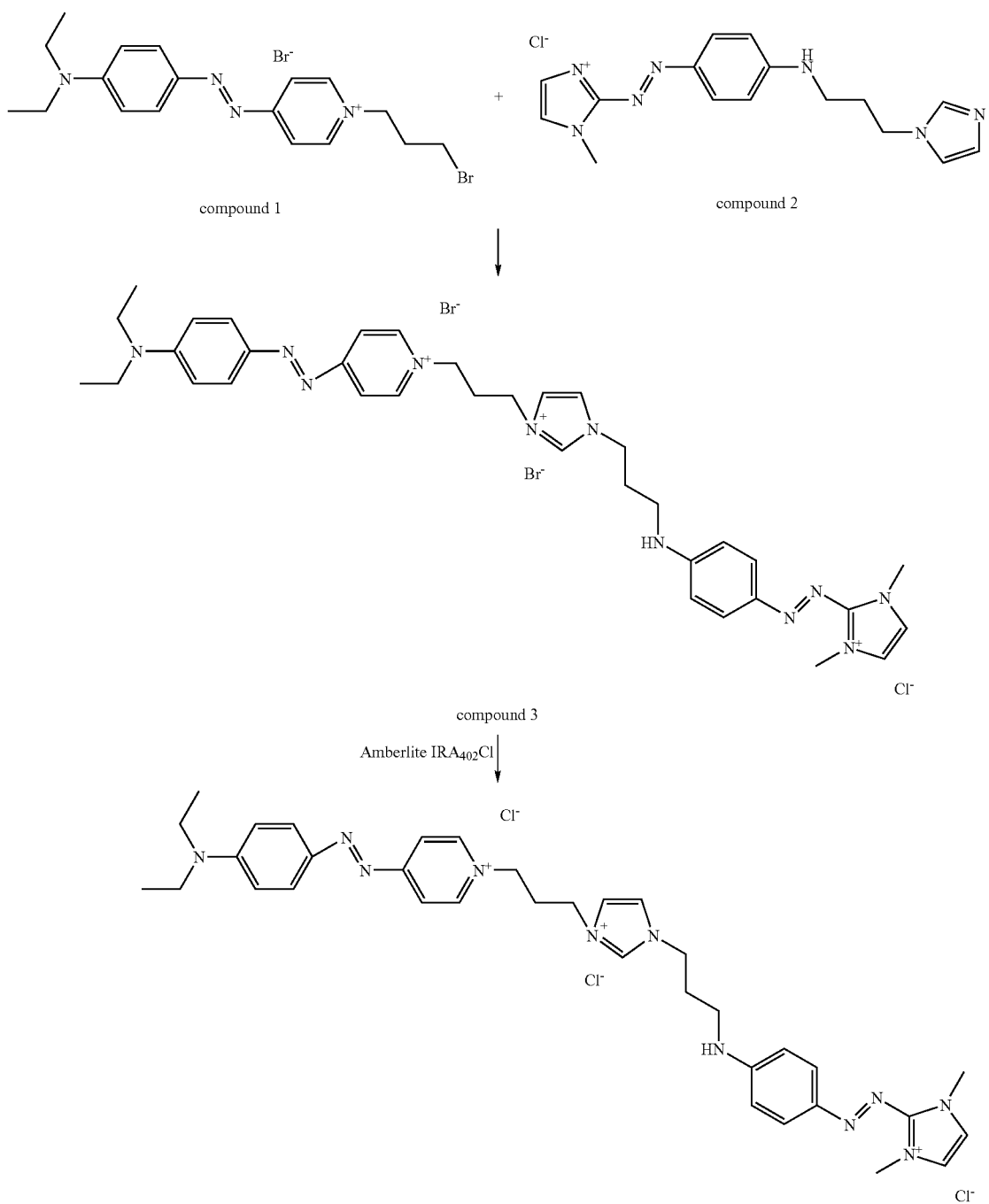

compound 1 + compound 2

↓ compound 3

Amberlite IRA$_{402}$Cl ↓

Procedure

One equivalent of azoimidazolium dye (compound 2) (5.23×10$^{-4}$ mol, 188.1 mg) was placed in 1.4 ml of anhydrous dimethylformamide in a three-necked flask, to which 0.1 equivalent of KI (5.23×10$^{-5}$ mol, 8.7 mg) was added.

The mixture was stirred under argon. One equivalent of azopyridinium dye (compound 1) (5.23×10$^{-4}$ mol, 238 mg) was then added.

Once the addition was complete, the mixture was heated to 90° C. (internal temperature).

After 24 hours, the heating was stopped and the reaction mixture was allowed to cool to room temperature. The reaction medium was then poured into 30 ml of ethyl acetate with stirring. A solid precipitated. The precipitate obtained was filtered off, rinsed with ethyl acetate, and dried under vacuum.

The solid was taken up in ethanol (10 ml per gram of resin) and then placed in contact, with stirring for 30 minutes, with an Amberlite IRA 402Cl exchange resin. The product obtained was filtered off, rinsed with ethanol, and dried under vacuum. A hygroscopic violet solid was then obtained.

The NMR and mass spectra were in accordance with the structure of the expected product. The UV-VIS spectrum exhibited 2 bands at 510 nm and 582 nm.

Example 2

Synthesis of the Following Compound

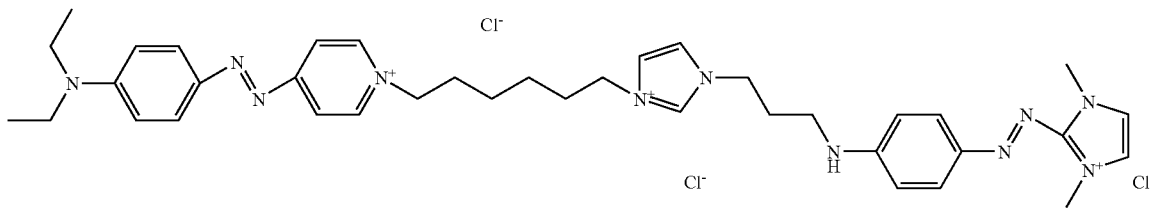

Synthetic Scheme and Procedure

The synthetic scheme and the procedure were similar to those described in Example 1.

Example 3

Dye Compositions

The composition below was prepared:

| Ingredients | Amount |
|---|---|
| (50/50 C8/C10) Alkyl polyglucoside (2) as a buffered 60% aqueous solution | 12 g |
| Pure absolute ethanol | 20 g |
| Pure benzyl alcohol | 4 g |
| Polyethylene glycol 400 (8 EO) | 6 g |
| Demineralized water | qs 100 g |

Two compositions were prepared, each comprising $5 \times 10^{-3}$ mol/l of each of the compounds obtained above.

The composition thus obtained was applied to locks of hair containing 90% white hairs. A strong dark purple shade was obtained with these two examples.

What is claimed is:

1. A cationic compound of formula (I), or the acid addition salts thereof:

Dye1-LK-Dye2      (I)

in which:

Dye1 and Dye2 represent:

Dye 1:

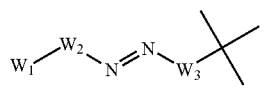

-continued

Dye 2:

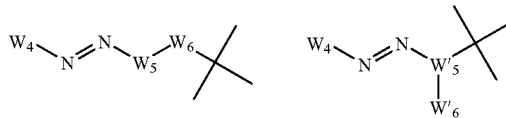

in which formulae:

$W_1$ and $W'_6$, independently of each other, are chosen from —$NR_1R_2$ and —$OR_3$, wherein $R_1$, $R_2$, and $R_3$, independently of each other, are chosen from hydrogen and saturated or unsaturated, aromatic or non-aromatic, optionally substituted $C_1$–$C_{20}$ hydrocarbon-based chains, which optionally form at least one optionally substituted 3- to 7-membered carbon-based ring, optionally interrupted with at least one entity chosen from hetero atoms and groups comprising at least one hetero atom;

$R_1$ and $R_2$ may optionally form, together with the nitrogen atom to which they are attached, an optionally substituted 5- or 7-membered heterocycle optionally comprising another nitrogen or non-nitrogen hetero atom; and $R_1$, $R_2$, and $R_3$, derived from $W'_6$, independently from each other, may optionally form, together with part of the group LK and the nitrogen or oxygen atom to which each is attached, a saturated or unsaturated, aromatic or non-aromatic, optionally substituted 5- to 7-membered heterocycle;

$W_6$ is chosen from —$NR'_1$— and —O—, wherein $R'_1$ is chosen from hydrogen and saturated or unsaturated, aromatic or non-aromatic, optionally substituted $C_1$–$C_{20}$ hydrocarbon-based chains, which optionally form at least one optionally substituted 3- to 7-membered carbon-based ring, optionally interrupted with at least one entity chosen from hetero atoms and groups comprising at least one hetero atom;

$R'_1$, derived from $W_6$, may optionally form, together with the nitrogen atom to which it is attached and part of the group LK, a saturated or unsaturated, aromatic or non-aromatic, optionally substituted 5- to 7-membered heterocycle optionally containing another hetero atom chosen from nitrogen and oxygen;

$W_2$, $W_5$, and $W'_5$, independently of each other, are chosen from formulae (a), (b), and (c) below:

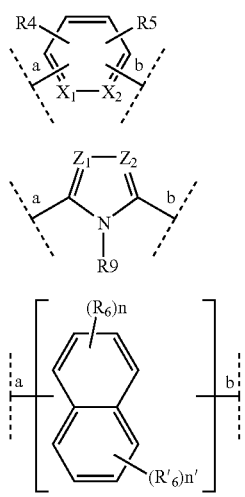

in which formulae:
X$_1$ is chosen from nitrogen and CR$_7$;
X$_2$ is chosen from nitrogen and CR$_8$;
Z$_1$ is chosen from nitrogen and CR$_{10}$; and
Z$_2$ is chosen from nitrogen and CR$_{11}$; wherein
R$_4$, R$_5$, R$_6$, R'$_6$, R$_7$, R$_8$, R$_{10}$, and R$_{11}$, independently of each other, are chosen from:
  linear or branched, saturated or unsaturated, aromatic or non-aromatic, optionally substituted C$_1$–C$_{16}$ hydrocarbon-based chains, which may form at least one optionally substituted 3- to 6-membered carbon-based ring, optionally interrupted with at least one entity chosen from hetero atoms and groups comprising at least one hetero atom;
  hydroxyl groups;
  C$_1$–C$_4$ alkoxy groups, C$_2$–C$_4$ (poly)hydroxyalkoxy groups; alkoxycarbonyl groups (RO—CO—) in which R represents a C$_1$–C$_4$ alkyl radical; alkylcarbonyloxy radicals (R$_a$CO—O—) in which R$_a$ represents a C$_1$–C$_4$ alkyl radical;
  amino groups, amino groups substituted with at least one C$_1$–C$_4$ alkyl radical, which may be identical or different, optionally comprising at least one hydroxyl group, the two alkyl radicals optionally forming, together with the nitrogen atom to which they are attached, a 5- or 6-membered heterocycle optionally comprising another nitrogen or non-nitrogen hetero atom; alkylcarbonylamino groups (R$_b$CO—NR$_b$—) in which the radicals R$_b$, independently of each other, are chosen fom C$_1$–C$_4$ alkyl radicals; carbamoyl groups ((R$_c$)$_2$N—CO) in which the radicals R$_c$, independently of each other, are chosen from hydrogen and C$_1$–C$_4$ alkyl radicals; ureido groups (N(R$_d$)$_2$—CO—NR'—) in which the radicals R$_d$ and R', independently of each other, are chosen from hydrogen and C$_1$–C$_4$ alkyl radicals; sulfonamide groups ((R$_e$)$_2$N—SO$_2$—) in which the radicals R$_e$, independently of each other, are chosen from hydrogen and C$_1$–C$_4$ alkyl radicals; alkylsulfonylamino group (R$_f$SO$_2$—NR$_a$'—) in which the radicals R$_f$ and R$_a$', independently of each other, are chosen from hydrogen and C$_1$–C$_4$ alkyl radicals; guanidinium groups ((R$_b$')$_2$N—C(=NH$_2^+$)—NR$_g$—) in which the radicals R$_g$ and R$_b$', independently of each other, are chosen from hydrogen and C$_1$–C$_4$ alkyl radicals;
  nitro groups; cyano groups; and halogen atoms;
R$_4$, R$_5$, R$_7$, R$_8$, R$_{10}$, and R$_{11}$ may represent hydrogen; or R$_4$, R$_5$, R$_6$, R'$_6$, R$_7$, R$_8$, R$_{10}$, and R$_{11}$, independently of each other, may optionally form, together with all or some of the groups W$_1$, W$_6$, and W'$_6$, a saturated or unsaturated, optionally substituted 5- to 7-membered heterocycle; or the bond from W$_2$ to W$_1$, from W$_5$ to W$_6$, or from W'$_5$ to W'$_6$ or to the group LK;
a represents the bond from W$_2$, W$_5$, or W'$_5$ to the azo group —N=N—;
b represents the bond from W'$_5$ to W'$_6$ or to the group LK;
R$_9$ is chosen from:
  hydrogen; and
  linear or branched, saturated or unsaturated, aromatic or non-aromatic, optionally substituted C$_1$–C$_{16}$ hydrocarbon-based chains, which may form at least one optionally substituted 3- to 7-membered carbon-based ring;
n and n' represent integers wherein the sum of n plus n' is less than or equal to 6;
W$_3$ and W$_4$, independently of each other, are chosen from cationic heteroaromatic radicals chosen from at least one of the formulae (1) to (11) below:

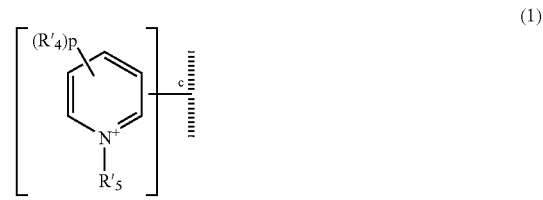

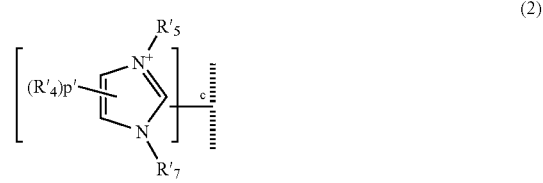

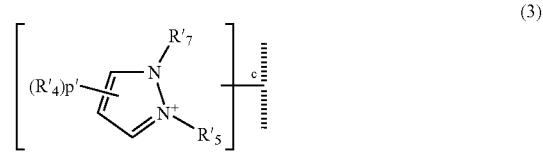

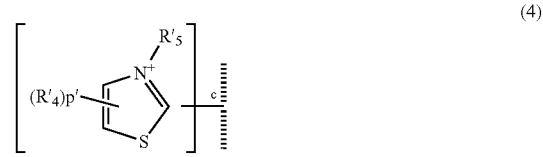

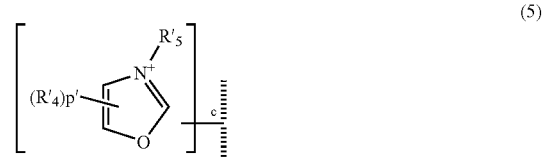

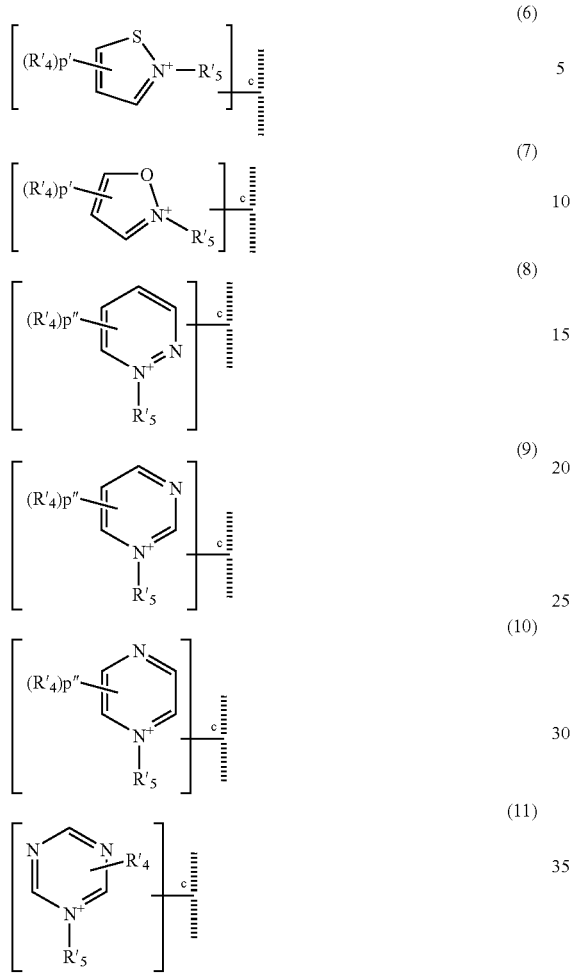

wherein:

R'$_4$, which may be identical or different, substituting the main ring, is chosen from:

- linear or branched, saturated or unsaturated, aromatic or non-aromatic, optionally substituted C$_1$–C$_{16}$ hydrocarbon-based chains, which may form at least one 3- to 6-membered carbon-based rings, optionally interrupted with at least one entity chosen from hetero atoms and groups comprising at least one hetero atom;
- hydroxyl groups;
- C$_1$–C$_4$ alkoxy groups, C$_2$–C$_4$ (poly)hydroxyalkoxy groups; alkoxycarbonyl groups (R$_h$O—CO—) in which R$_h$ represents a C$_1$–C$_4$ alkyl radical, alkylcarbonyloxy radicals (R$_i$CO—O—) in which R$_i$ represents a C$_1$–C$_4$ alkyl radical;
- amino groups, amino groups substituted with at least one C$_1$–C$_4$ alkyl radical, independently of each other, optionally comprising at least one hydroxyl group, the two alkyl radicals optionally forming, together with the nitrogen atom to which they are attached, a 5- or 6-membered heterocycle optionally comprising another nitrogen or non-nitrogen hetero atom; alkylcarbonylamino groups (R$_j$CO—NR$_c$'—) in which the radical R$_j$ represents a C$_1$–C$_4$ alkyl radical, and the radical R$_c$' is chosen from hydrogen and C$_1$–C$_4$ alkyl radicals; a carbamoyl group ((R$_k$)$_2$N—CO—) in which the radicals R$_k$, independently of each other, are chosen from hydrogen and C$_1$–C$_4$ alkyl radicals; ureido groups (N(R$_L$)$_2$—CO—NR$_d$'—) in which the radicals R$_L$ and R$_d$', independently of each other, are chosen from hydrogen and C$_1$–C$_4$ alkyl radicals; sulfonamide groups ((R$_m$)$_2$N—SO$_2$—) in which the radicals R$_m$, independently of each other, are chosen from hydrogen and C$_1$–C$_4$ alkyl radicals; alkylsulfonylamino groups (R$_n$SO$_2$—NR$_e$'—) in which the radicals R$_n$ and R$_e$', independently of each other, are chosen from hydrogen and C$_1$–C$_4$ alkyl radicals; guanidinium groups ((R$_f$')$_2$N—C(=NH$_2$$^+$)—NR$_p$—) in which the radicals R$_p$ and R$_f$', independently of each other, are chosen from hydrogen and C$_1$–C$_4$ alkyl radicals;

nitro groups; cyano groups; and halogen atoms;

two radicals R'$_4$ borne by two adjacent carbon atoms of the main ring may optionally form an aromatic or non-aromatic, 5- or 6-membered secondary ring, optionally substituted with at least one entity chosen from hydrogen; hydroxyl groups; C$_1$–C$_4$ alkyl radicals; C$_1$–C$_4$ alkoxy radicals; C$_2$–C$_4$ (poly)hydroxyalkoxy radicals; amino radicals; amino radicals substituted with at least one C$_1$–C$_4$ alkyl radical, which may be identical or different, optionally comprising at least one hydroxyl group;

R'$_5$, borne by the quaternized nitrogen atom, in the case of W$_4$, is chosen from linear or branched, saturated or unsaturated, aromatic or non-aromatic, optionally substituted C$_1$–C$_{16}$ hydrocarbon-based chains, which optionally form at least one optionally substituted 3- to 6-membered carbon-based rings, optionally interrupted with at least one entity chosen from hetero atoms and groups comprising at least one hetero atom; wherein the radical R'$_5$ is such that the atom directly linked to the quaternized nitrogen atom is a carbon atom;

R'$_5$ borne by the quaternized nitrogen atom, in the case of W$_3$, represents a bond to LK;

R'$_7$ is chosen from optionally substituted C$_1$–C$_4$ alkyl radicals; optionally substituted phenyl radicals; and optionally substituted benzyl radicals; the bond c links the cationic radical defined by formulae (1) to (11) to the azo group; wherein the bond may be on the main or secondary ring;

p is an integer ranging from 0 to 4;

p' is an integer ranging from 0 to 2;

p" is an integer ranging from 0 to 3; and when the main ring does not bear the maximum number of substituents, then the unsubstituted position bears a nitrogen atom; and LK is chosen from saturated or unsaturated, linear or branched, cyclic or non-cyclic, aromatic or non-aromatic, optionally substituted C$_2$–C$_{40}$ hydrocarbon-based chains, bearing at least one cationic charge, optionally interrupted with at least one entity chosen from hetero atoms and groups comprising at least one hetero atom; wherein if LK is linked to W'$_5$, LK may end with at least one entity chosen from hetero atoms and groups comprising at least one hetero atom;

if LK is linked to $W'_6$, LK may end with a group comprising at least one hetero atom chosen from —CO— and —SO$_2$—; and if LK is linked to $W_3$, the bonding takes place via a carbon atom; and the electrical neutrality of the compounds is ensured by at least one cosmetically acceptable anion An.

2. The compound of claim 1, wherein $R_1$, $R_2$, $R_3$, and $R'_1$, independently of each other, are chosen from optionally substituted $C_1$–$C_{16}$ hydrocarbon-based chains.

3. The compound of claim 1, wherein the hetero atoms in each instance are chosen from oxygen and nitrogen.

4. The compound of claim 1, wherein the halogen atoms in each instance are chosen from chlorine and fluorine.

5. The compound of claim 1, wherein LK is chosen from saturated or unsaturated, linear or branched, cyclic or non-cyclic, aromatic or non-aromatic, optionally substituted $C_2$–$C_{20}$ hydrocarbon-based chains.

6. The compound of claim 1, wherein when the two radicals $R'_4$ borne by two adjacent carbon atoms of the main ring form a 6-membered aromatic secondary ring optionally substituted with at least one entity chosen from hydrogen, hydroxyl groups, $C_1$–$C_4$ alkyl radicals, $C_1$–$C_4$ alkoxy radicals, $C_2$–$C_4$(poly)hydroxyalkoxy radicals, amino radicals, amino radicals substituted with at least one C1–C4 alkyl radicals, which may be identical or different, optionally comprising at least one hydroxyl group.

7. The compound of claim 1, wherein in the formulae (1) to (11), the bond c with the azo group is on the main ring.

8. The compound of claim 1, wherein $R_1$, $R_2$, $R_3$, and $R'_1$, independently of each other, are chosen from:
hydrogen;
optionally substituted $C_1$–$C_6$ alkyl radicals; and
optionally substituted aryl and arylalkyl radicals; and wherein $R_1$, $R_2$, and $R_3$, derived from $W'_6$, independently from each other, may optionally form, together with part of the group LK and with the nitrogen or oxygen atom to which each is attached, a saturated or unsaturated, aromatic or non-aromatic, optionally substituted 5- to 7-membered heterocycle; and $R'_1$, derived from $W_6$, may optionally form, together with the nitrogen atom to which it is attached and part of the group LK, a saturated or unsaturated, aromatic or non-aromatic, optionally substituted 5-, 6-, or 7-membered heterocycle optionally containing another hetero atom chosen from nitrogen and oxygen.

9. The compound of claim 8, wherein the optionally substituted aryl and arylalkyl radicals are chosen from phenyl and benzyl.

10. The compound of claim 1, wherein $R_1$, $R_2$, $R_3$, and $R'_1$, which may be identical or different, are chosen from:
hydrogen;
optionally substituted $C_1$–$C_3$ alkyl radicals;
phenyl radicals, optionally substituted with at least one radical chosen from hydroxyl radicals, $C_1$–$C_2$ alkoxy radicals, amino radicals, and amino radicals substituted with at least one $C_1$–$C_4$ group optionally comprising at least one hydroxyl group; wherein
radicals $R'_1$, derived from $W_6$, may form, together with the nitrogen atom to which they are attached and part of the group LK, a 5- or 6-membered heterocycle chosen from pyrrolidine, piperidine, piperazine and homopiperazine heterocycles optionally substituted with at least one radical chosen from methyl, hydroxyl, amino, and (di)methylamino radicals.

11. The compound of claim 10, wherein the optionally substituted $C_1$–$C_3$ alkyl radicals are chosen from methyl, ethyl, 2-hydroxyethyl, and 2-methoxyethyl radicals.

12. The compound of claim 1, wherein $R_1$, $R_2$, $R_3$, and $R_1'$, which may be identical or different, are chosen from:
hydrogen;
methyl, ethyl, and 2-hydroxyethyl radicals; and
phenyl radicals, optionally substituted with at least one radical chosen from hydroxyl, methoxy, amino, (di)methylamino, and (di)(2-hydroxyethyl)amino radicals; and wherein radicals $R'_1$ derived from $W_6$ may form, together with the nitrogen atom to which they are attached and part of the group LK, a 5- to 7-membered heterocycle.

13. The compound of claim 12, wherein the 5- to 7-membered heterocycle is chosen from pyrrolidine, 3-hydroxypyrrolidine, 3-dimethylaminopyrrolidine, piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine, and 1-methyl-1,4-perhydrodiazepine.

14. The compound of claim 1, wherein $R_4$, $R_5$, $R_6$, $R'_6$, $R_7$, $R_8$, $R_9$, $R_{10}$, and $R_{11}$, which may be identical or different, are chosen from:
optionally substituted $C_1$–$C_{16}$ alkyl radicals;
halogen atoms;
hydroxyl groups;
$C_1$–$C_2$ alkoxy radicals; $C_2$–$C_4$ (poly)hydroxyalkoxy radicals;
amino radicals; amino radicals substituted with one or two $C_1$–$C_4$ alkyl radicals, which may be identical or different, optionally comprising at least one entity chosen from hydroxyl groups or $C_1$–$C_4$ dialkylamino groups;
alkylcarbonylamino radicals ($R_bCO$—$NR_{b1}$—) in which the radical Rb represents a $C_1$–$C_4$ alkyl radical and the radical $R_{b1}$ is chosen from hydrogen and $C_1$–$C_4$ alkyl radicals; carbamoyl radicals (($R_c$)$_2$N—CO—) in which the radicals $R_c$, which may be identical or different, are chosen from hydrogen and $C_1$–$C_4$ alkyl radicals optionally comprising at least one hydroxyl group; alkylsulfonylamino radicals ($R_fSO_2$—$NR_a'$—) in which the radical $R_a'$ is chosen from hydrogen and $C_1$–$C_4$ alkyl radicals optionally comprising at least one hydroxyl group, and the radical $R_f$ represents a $C_1$–$C_4$ alkyl radical; aminosulfonyl radicals (($R_e$)$_2$N—SO$_2$—) in which the radicals $R_e$, which may be identical or different, are chosen from hydrogen atom and $C_1$–$C_4$ alkyl radicals optionally comprising at least one hydroxyl group; and
bonds from $W'_5$ to $W'_6$; and $R_4$, $R_5$, $R_7$, $R_8$, $R_{10}$, and $R_{11}$ may optionally represent hydrogen.

15. The compound of claim 14, wherein $R_4$, $R_5$, $R_6$, $R'_6$, $R_7$, $R_8$, $R_9$, $R_{10}$, and $R_{11}$, which may be identical or different, are chosen from optionally substituted $C_1$–$C_8$ alkyl radicals.

16. The compound of claim 14, wherein the halogen atoms are chosen from chlorine, fluorine, and bromine.

17. The compound of claim 1, wherein $R_4$, $R_5$, $R_6$, $R'_6$, $R_7$, $R_8$, $R_9$, $R_{10}$, and $R_{11}$, which may be identical or different, are chosen from:
$C_1$–$C_4$ alkyl radicals optionally substituted with at least one radical chosen from hydroxyl radicals, acylamino radicals, and amino radicals substituted with two identical or different $C_1$–$C_2$ alkyl radicals, optionally comprising at least one hydroxyl group, and $C_1$–$C_2$ alkoxy radicals;

amino radicals; amino radicals substituted with one or two identical or different $C_1$–$C_2$ alkyl radicals, optionally comprising at least one hydroxyl group; acylamino radicals; carbamoyl radicals; sulfonylamino radicals;

hydroxyl radicals; $C_1$–$C_2$ alkoxy radicals; and bonds from $W'_5$ to $W'_6$; and $R_4$, $R_5$, $R_7$, $R_8$, $R_{10}$, and $R_{11}$ may optionally represent hydrogen.

18. The compound of claim 1, wherein $W_2$, $W_5$, and $W'_5$, which may be identical or different, are chosen from

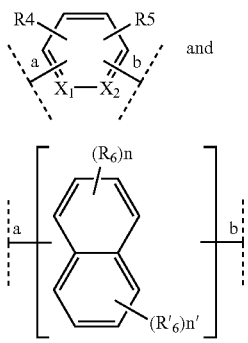

19. The compound of claim 1, wherein $X_1$ represents $CR_7$.

20. The compound of claim 19, wherein $X_2$ represents $CR_8$.

21. The compounds of claim 1, wherein $W_3$ and $W_4$, independently of each other, may be chosen from formulae (1), (2), and (3):

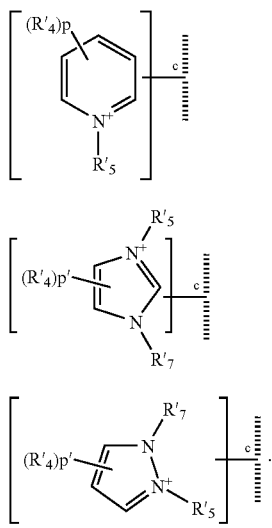

22. The compound of claim 21, wherein the aromatic heterocycle is chosen from 2-imidazolium, 2-benzimidazolium, 2-pyridinium, 3-pyridinium, 4-pyridinium, 2-quinolinium, 4-quinolinium, 3-pyrazolium, 4-pyrazolium, 3-indazolium, 4-indazolium, 5-indazolium, 6-indazolium and 7-indazolium; and at least one of the groups $W_3$ and $W_4$ does not represent an unsubstituted imidazolium group.

23. The compound of claim 1, wherein LK represents the following formula:

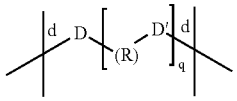

in which

D and D', independently of each other, represent linear or branched, saturated or unsaturated $C_1$–$C_{14}$ hydrocarbon-based bonds, optionally interrupted with at least one entity chosen from hetero atoms and groups comprising at least one hetero atom;

the bond d links the arms D and D' to the groups $W_3$, $W_6$, and $W'_5$;

q is greater than or equal to 1;

R is chosen from formulae (d), (e), and (f):

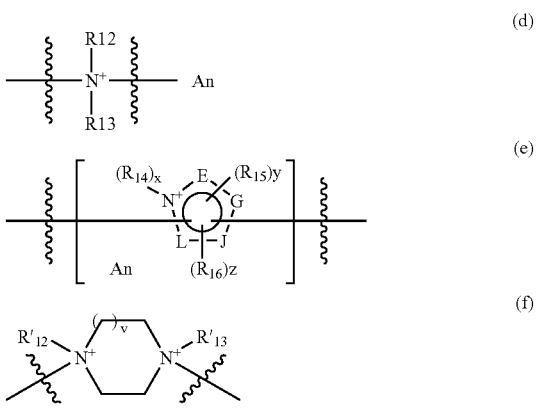

wherein $R_{12}$, $R_{13}$, $R'_{12}$, and $R'_{13}$, independently of each other, are chosen from $C_1$–$C_{15}$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals; arylalkyl radicals; $C_1$–$C_6$ amidoalkyl radicals; $C_1$–$C_6$ aminoalkyl radicals; $C_1$–$C_6$ aminoalkyl radicals in which the amine is substituted with at least one identical or different $C_1$–$C_4$ alkyl group, ($C_1$–$C_6$)alkylcarbonyl radicals, acylamino radicals, and ($C_1$–$C_6$)alkylsulfonyl radicals;

or $R_{12}$ and $R_{13}$ may form, together with the nitrogen atom to which they are attached, a 5-, 6-, or 7-membered saturated cationic ring that may contain at least one hetero atom, the cationic ring optionally being substituted with an entity chosen from halogen atoms; hydroxyl radicals; $C_1$–$C_6$ alkyl radicals; $C_1$–$C_6$ monohydroxyalkyl radicals; $C_2$–$C_6$ polyhydroxyalkyl radicals; $C_1$–$C_6$ alkoxy radicals; amido radicals; ($C_1$–$C_6$) alkylcarbonyl radicals; thio radicals; $C_1$–$C_6$ thioalkyl radicals; ($C_1$–$C_6$)alkylthio radicals; amino radicals; and amino radicals substituted with at least one radical chosen from $C_1$–$C_6$ alkyl radicals, ($C_1$–$C_6$)-alkylcarbonyl radicals, acylamino radicals, and ($C_1$–$C_6$)alkylsulfonyl radicals; $R_{12}$ or $R_{13}$ may form, together with D or D', a 5-, 6-, or 7-membered saturated cationic ring that may contain at least one hetero atom, the cationic ring optionally being substituted with an entity chosen from halogen atoms; hydroxyl radicals; $C_1$–$C_6$ alkyl radicals; $C_1$–$C_6$ monohydroxyalkyl radicals; $C_2$–$C_6$ poly-hydroxyalkyl radicals; $C_1$–$C_6$ alkoxy radicals; amido radicals; ($C_1$–$C_6$)alkylcarbonyl radicals; thio radicals; $C_1$–$C_6$ thioalkyl radicals; ($C_1$–$C_6$)alkylthio radicals; amino radicals; and amino radicals substituted with at least one radical chosen from $C_1$–$C_6$ alkyl radicals, ($C_1$–$C_6$)alkylcarbonyl radicals, acylamino radicals, and ($C_1$–$C_6$)alkylsulfonyl radicals;

or $R_{12}$ and $R_{13}$ may form, together with $W_1$ or $W_6$, a 5-, 6-, or 7-membered, saturated or unsaturated, aromatic or non-aromatic, optionally substituted cationic heterocycle;

the ring members E, G, J, and L, which may be identical or different, are chosen from carbon, oxygen, sulfur, and nitrogen such that they may form a ring chosen from pyrazolium, imidazolium, triazolium, oxazolium, isoxazolium, thiazolium, and isothiazolium rings, $R_{14}$ has the same meaning as $R_{12}$, independently of $R_{12}$;

$R_{15}$ is chosen from $C_1$–$C_6$ alkyl radicals; $C_2$–$C_6$ monohydroxyalkyl radicals, $C_1$–$C_6$ polyhydroxyalkyl radicals, ($C_1$–$C_6$)alkoxy($C_1$–$C_6$)alkyl radicals, $C_2$–$C_6$ carbamylalkyl radicals, ($C_1$–$C_6$)alkylcarboxy($C_1$–$C_6$) alkyl radicals, and benzyl radicals, wherein $R_{15}$ is borne by a nitrogen atom;

$R_{16}$, which may be identical or different, is chosen from hydrogen; halogen atoms; $C_1$–$C_6$ alkyl radicals; $C_1$–$C_6$ monohydroxyalkyl radicals; $C_2$–$C_6$ polyhydroxyalkyl radicals; $C_1$–$C_6$ alkoxy radicals; amido radicals; carboxyl radical; $C_1$–$C_6$ alkylcarbonyl radicals; $C_1$–$C_6$ thioalkyl radicals; ($C_1$–$C_6$)alkylthio radicals; amino radicals disubstituted with at least one radical chosen from ($C_1$–$C_6$)alkyl radicals, ($C_1$–$C_6$)alkylcarbonyl radicals, and ($C_1$–$C_6$)alkylsulfonyl radicals; benzyl radicals, phenyl radicals optionally substituted with at least one radical chosen from methyl, hydroxyl, amino, and methoxy radicals; wherein the radicals $R_{16}$ are borne by a carbon atom;

An is chosen from organic and mineral anions;
z is an integer ranging from 1 to 3;
y is equal to 0 or 1;
v is an integer equal to 1 or 2; and
x is equal to 0 or 1; wherein
when x is 0, one of the linker arms D or D' is attached to the quaternized nitrogen atom; and
when x is 1, at least one of the linker arms D and/or D' is attached to a carbon atom.

24. The compound of claim 23, wherein the hetero atoms in D and D' are chosen from oxygen and nitrogen.

25. The compound of claim 23, wherein D and D', which may be identical or different, are chosen from unsubstituted $C_1$–$C_6$ alkyl chains.

26. The compound of claim 23, wherein q is equal to 1 or 2.

27. The compound of claim 23, wherein, in formula (d), $R_{12}$ and $R_{13}$, which may be identical or different, are chosen from $C_1$–$C_6$ alkyl radicals, $C_1$–$C_4$ monohydroxyalkyl radicals, $C_2$–$C_4$ polyhydroxyalkyl radicals, ($C_1$–$C_6$)alkoxy($C_2$–$C_4$)alkyl radicals, $C_2$–$C_6$ amidoalkyl radicals, and $C_2$–$C_6$ dimethylaminoalkyl radicals.

28. The compound of claim 27, wherein D and D', which may be identical or different are chosen from substituted and unsubstituted $C_1$–$C_6$ alkyl chains.

29. The compound of claim 23, wherein, in formula (e), the ring members E, G, J, and L form a ring chosen from imidazolium, pyrazolium, oxazolium, and thiazolium rings; and
x and b are equal to 0.

30. The compound of claim 29, wherein D and D', which may be identical or different, are chosen from substituted and unsubstituted $C_1$–$C_4$ alkyl chains.

31. The compound of claim 29, wherein $R_{14}$ is chosen from methyl, ethyl, and 2-hydroxyethyl radicals.

32. The compound of claim 23, wherein, in formula (f), $R'_{12}$ and $R'_{13}$, which may be identical or different, are chosen from $C_1$–$C_6$ alkyl radicals, $C_1$–$C_4$ monohydroxyalkyl radicals, $C_2$–$C_4$ polyhydroxyalkyl radicals, ($C_1$–$C_6$)alkoxy($C_2$–$C_4$)alkyl radicals; $C_2$–$C_6$ amidoalkyl radicals, and $C_2$–$C_6$ dimethylaminoalkyl radicals.

33. The compound of claim 32, wherein D and D', which may be identical or different, are chosen from substituted and unsubstituted $C_1$–$C_6$ alkyl chains.

34. The compound of claim 32, wherein v is equal to 1.

35. The compound of claim 1, wherein the compound is chosen from the following formulae:

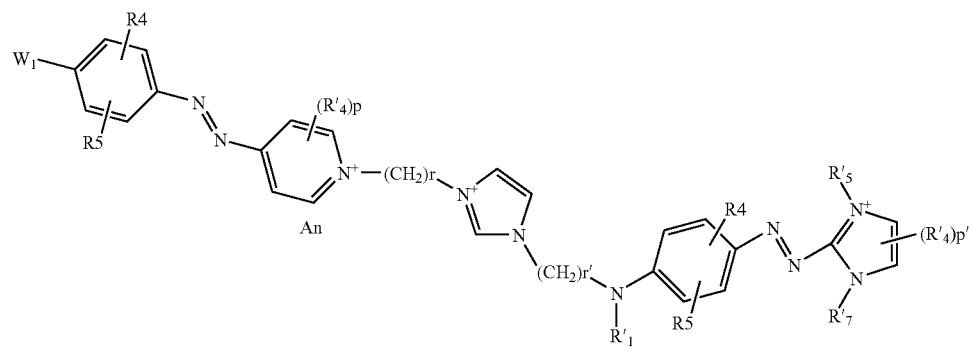

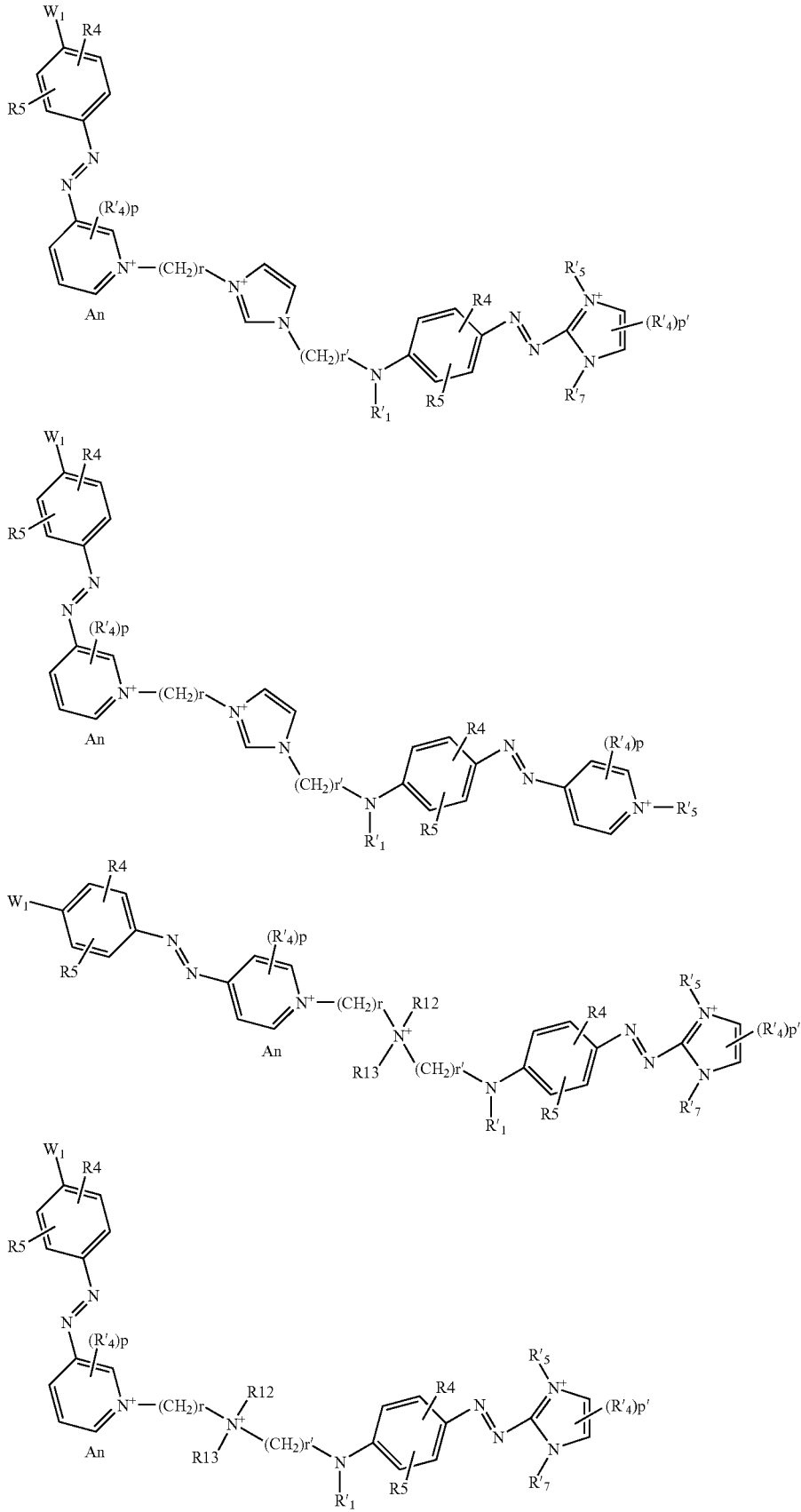

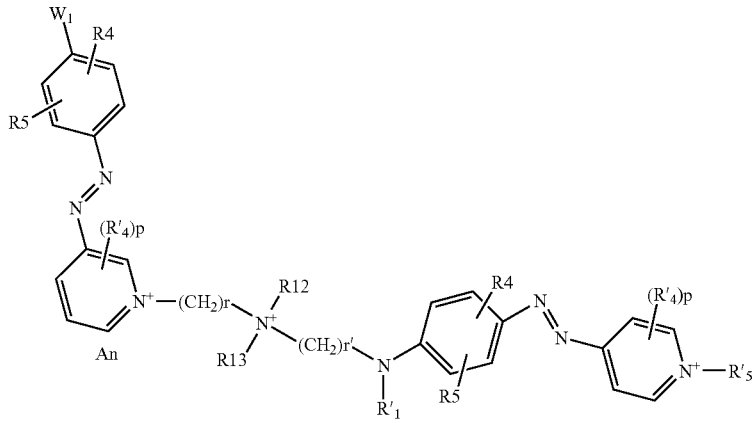

wherein
r and r', which may be identical or different, are integers ranging from 1 to 10; and
the electrical neutrality of the molecule is respected by the presence of at least one cosmetically acceptable anion An.

36. The compound of claim 35, wherein r and r', which may be identical or different, are integers ranging from 1 to 6.

37. The compound of claim 1, wherein the cosmetically acceptable anion is chosen from halides; hydroxides; sulfates; hydrogen sulfates; ($C_1$–$C_6$)alkyl sulfates; phosphates; carbonates; hydrogen carbonates; perchlorates; acetates; tartrates; citrates; oxalates; ($C_1$–$C_6$)alkylsulfonates; and arylsulfonates, which are unsubstituted or substituted with a $C_1$–$C_4$ alkyl radical.

38. The compound of claim 37, wherein the halides are chosen from chlorides, bromides, fluorides, and iodides.

39. The compound of claim 37, wherein the ($C_1$–$C_6$) alkylsulfonates are methylsulfonate.

40. The compound of claim 37, wherein the arylsulfonate is 4-tolylsulfonate.

41. A dye composition comprising, in a medium that is suitable for dyeing keratin fibers, at least one cationic compound of formula (I), or an acid addition salt thereof, Dye1-LK-Dye2      (I)

in which:
Dye1 and Dye2 represent:

Dye 1:

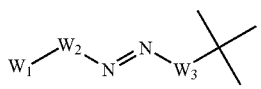

Dye 2:

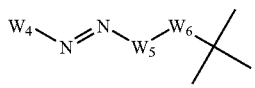

-continued

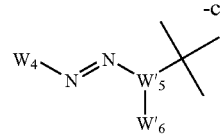

in which formulae:
$W_1$ and $W'_6$, independently of each other, are chosen from —$NR_1R_2$ and —$OR_3$, wherein
$R_1$, $R_2$, and $R_3$, independently of each other, are chosen from hydrogen and saturated or unsaturated, aromatic or non-aromatic, optionally substituted $C_1$–$C_{20}$ hydrocarbon-based chains, which optionally form at least one optionally substituted 3- to 7-membered carbon-based ring, optionally interrupted with at least one entity chosen from hetero atoms and groups comprising at least one hetero atom;
$R_1$ and $R_2$ may optionally form, together with the nitrogen atom to which they are attached, an optionally substituted 5- or 7-membered heterocycle optionally comprising another nitrogen or non-nitrogen hetero atom; and
$R_1$, $R_2$, and $R_3$, derived from $W'_6$, independently from each other, may optionally form, together with part of the group LK and the nitrogen or oxygen atom to which each is attached, a saturated or unsaturated, aromatic or non-aromatic, optionally substituted 5- to 7-membered heterocycle;
$W_6$ is chosen from —$NR'_1$— and —O—,
wherein
$R'_1$ is chosen from hydrogen and saturated or unsaturated, aromatic or non-aromatic, optionally substituted $C_1$–$C_{20}$ hydrocarbon-based chains, which optionally form at least one optionally substituted 3- to 7-membered carbon-based ring, optionally interrupted with at least one entity chosen from hetero atoms and groups comprising at least one hetero atom;
$R'_1$, derived from $W_6$, may optionally form, together with the nitrogen atom to which it is attached and part of the group LK, a saturated or unsaturated, aromatic or non-aromatic, optionally substituted 5- to 7-membered heterocycle optionally containing another hetero atom chosen from nitrogen and oxygen;

$W_2$, $W_5$, and $W'_5$, independently of each other, are chosen from formulae (a), (b), and (c) below:

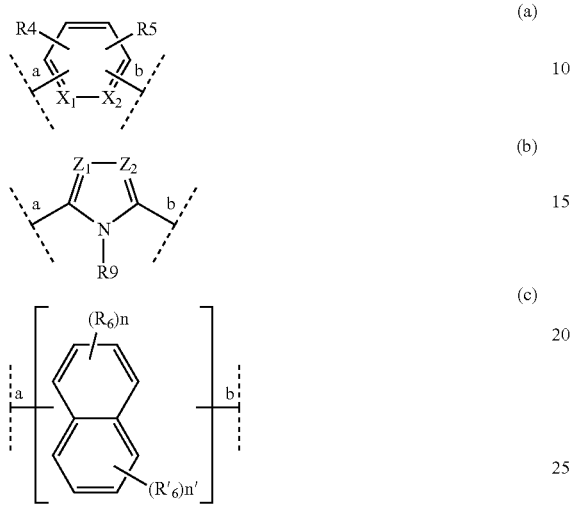

in which formulae:

$X_1$ is chosen from nitrogen and $CR_7$;
$X_2$ is chosen from nitrogen and $CR_8$;
$Z_1$ is chosen from nitrogen and $CR_{10}$; and
$Z_2$ is chosen from nitrogen and $CR_{11}$; wherein
$R_4$, $R_5$, $R_6$, $R'_6$, $R_7$, $R_8$, $R_{10}$, and $R_{11}$, independently of each other, are chosen from:

linear or branched, saturated or unsaturated, aromatic or non-aromatic, optionally substituted $C_1$–$C_{16}$ hydrocarbon-based chains, which may form at least one optionally substituted 3- to 6-membered carbon-based ring, optionally interrupted with at least one entity chosen from hetero atoms and groups comprising at least one hetero atom;

hydroxyl groups;

$C_1$–$C_4$ alkoxy groups, $C_2$–$C_4$ (poly)hydroxyalkoxy groups; alkoxycarbonyl groups (RO—CO—) in which R represents a $C_1$–$C_4$ alkyl radical; alkylcarbonyloxy radicals ($R_a$CO—O—) in which $R_a$ represents a $C_1$–$C_4$ alkyl radical;

amino groups, amino groups substituted with at least one $C_1$–$C_4$ alkyl radical, which may be identical or different, optionally comprising at least one hydroxyl group, the two alkyl radicals optionally forming, together with the nitrogen atom to which they are attached, a 5- or 6-membered heterocycle optionally comprising another nitrogen or non-nitrogen hetero atom; alkylcarbonylamino groups ($R_b$CO—$NR_b$—) in which the radicals $R_b$, independently of each other, are chosen from $C_1$–$C_4$ alkyl radicals; carbamoyl groups (($R_c$)$_2$N—CO) in which the radicals $R_c$, independently of each other, are chosen from hydrogen and $C_1$–$C_4$ alkyl radicals; ureido groups (N($R_d$)$_2$—CO—NR'—) in which the radicals $R_d$ and R', independently of each other, are chosen from hydrogen and $C_1$–$C_4$ alkyl radicals; sulfonamide groups (($R_e$)$_2$N—$SO_2$—) in which the radicals $R_e$, independently of each other, are chosen from hydrogen and $C_1$–$C_4$ alkyl radicals; alkylsulfonylamino group ($R_f SO_2$—$NR_a'$—) in which the radicals $R_f$ and $R_a'$, independently of each other, are chosen from hydrogen and $C_1$–$C_4$ alkyl radicals; guanidinium groups (($R_b'$)$_2$N—C(=$NH_2^+$)—$NR_g$—) in which the radicals $R_g$ and $R_b'$, independently of each other, are chosen from hydrogen and $C_1$–$C_4$ alkyl radicals;

nitro groups; cyano groups; and halogen atoms;

$R_4$, $R_5$, $R_7$, $R_8$, $R_{10}$, and $R_{11}$ may represent hydrogen; or $R_4$, $R_5$, $R_6$, $R'_6$, $R_7$, $R_8$, $R_{10}$, and $R_{11}$, independently of each other, may optionally form, together with all or some of the groups $W_1$, $W_6$, and $W'_6$, a saturated or unsaturated, optionally substituted 5- to 7-membered heterocycle; or the bond from $W_2$ to $W_1$, from $W_5$ to $W_6$, or from $W'_5$ to $W'_6$ or to the group LK;

a represents the bond from $W_2$, $W_5$, or $W'_5$ to the azo group —N=N—;

b represents the bond from $W'_5$ to $W'_6$ or to the group LK;

$R_g$ is chosen from:

hydrogen; and linear or branched, saturated or unsaturated, aromatic or non-aromatic, optionally substituted $C_1$–$C_{16}$ hydrocarbon-based chains, which may form at least one optionally substituted 3- to 7-membered carbon-based ring;

n and n' represent integers wherein the sum of n plus n' is less than or equal to 6;

$W_3$ and $W_4$, independently of each other, are chosen from cationic heteroaromatic radicals chosen from at least one of the formulae (1) to (11) below:

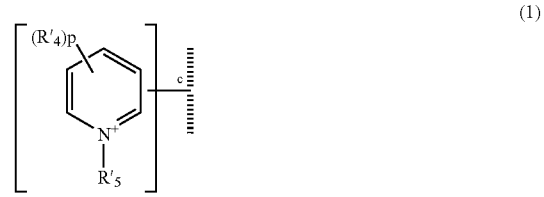

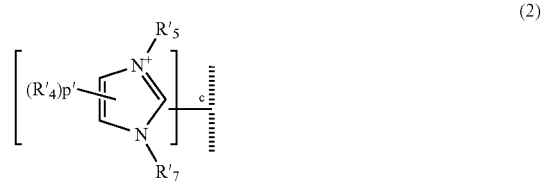

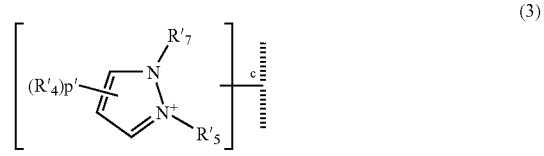

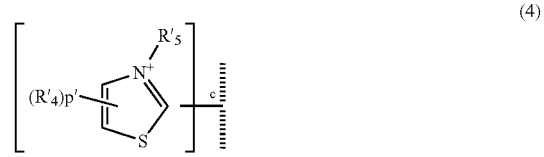

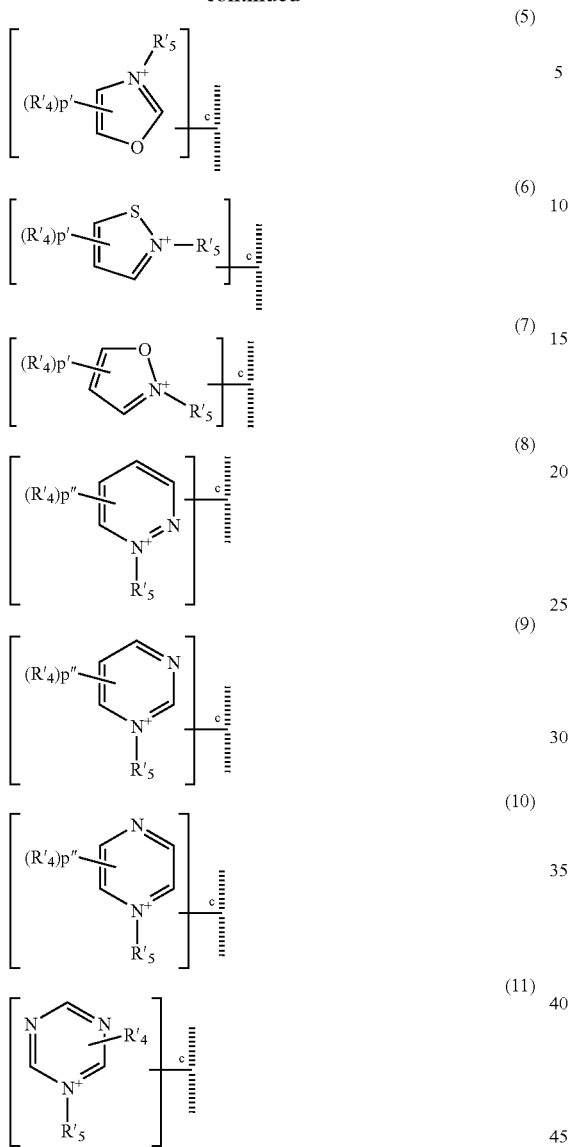

wherein:

R'₄, which may be identical or different, substituting the main ring, is chosen from:

- linear or branched, saturated or unsaturated, aromatic or non-aromatic, optionally substituted $C_1$–$C_{16}$ hydrocarbon-based chains, which may form at least one 3- to 6-membered carbon-based rings, optionally interrupted with at least one entity chosen from hetero atoms and groups comprising at least one hetero atom;
- hydroxyl groups;
- $C_1$–$C_4$ alkoxy groups, $C_2$–$C_4$ (poly)hydroxyalkoxy groups; alkoxycarbonyl groups ($R_h$O—CO—) in which $R_h$ represents a $C_1$–$C_4$ alkyl radical, alkylcarbonyloxy radicals ($R_i$CO—O—) in which $R_i$ represents a $C_1$–$C_4$ alkyl radical;
- amino groups, amino groups substituted with at least one $C_1$–$C_4$ alkyl radical, independently of each other, optionally comprising at least one hydroxyl group, the two alkyl radicals optionally forming, together with the nitrogen atom to which they are attached, a 5- or 6-membered heterocycle optionally comprising another nitrogen or non-nitrogen hetero atom; alkylcarbonylamino groups ($R_j$CO—NR$_c$'—) in which the radical $R_j$ represents a $C_1$–$C_4$ alkyl radical, and the radical $R_c$' is chosen from hydrogen and $C_1$–$C_4$ alkyl radicals; a carbamoyl group (($R_k$)₂N—CO—) in which the radicals $R_k$, independently of each other, are chosen from hydrogen and $C_1$–$C_4$ alkyl radicals; ureido groups (N($R_L$)₂—CO—NR$_d$'—) in which the radicals $R_L$ and $R_d$', independently of each other, are chosen from hydrogen and $C_1$–$C_4$ alkyl radicals; sulfonamide groups (($R_m$)₂N—SO₂—) in which the radicals $R_m$, independently of each other, are chosen from hydrogen and $C_1$–$C_4$ alkyl radicals; alkylsulfonylamino groups ($R_n$SO₂—NR$_e$'—) in which the radicals $R_n$ and $R_e$', independently of each other, are chosen from hydrogen and $C_1$–$C_4$ alkyl radicals; guanidinium groups (($R_f$)₂N—C(=NH₂⁺)—NR$_p$—) in which the radicals $R_p$ and $R_f$', independently of each other, are chosen from hydrogen and $C_1$–$C_4$ alkyl radicals;
- nitro groups; cyano groups; and halogen atoms;
- two radicals R'₄ borne by two adjacent carbon atoms of the main ring may optionally form an aromatic or non-aromatic, 5- or 6-membered secondary ring, optionally substituted with at least one entity chosen from hydrogen; hydroxyl groups; $C_1$–$C_4$ alkyl radicals; $C_1$–$C_4$ alkoxy radicals; $C_2$–$C_4$ (poly)hydroxyalkoxy radicals; amino radicals; amino radicals substituted with at least one $C_1$–$C_4$ alkyl radical, which may be identical or different, optionally comprising at least one hydroxyl group;

R'₅, borne by the quaternized nitrogen atom, in the case of W₄, is chosen from linear or branched, saturated or unsaturated, aromatic or non-aromatic, optionally substituted $C_1$–$C_{16}$ hydrocarbon-based chains, which optionally form at least one optionally substituted 3- to 6-membered carbon-based rings, optionally interrupted with at least one entity chosen from hetero atoms and groups comprising at least one hetero atom; wherein the radical R'₅ is such that the atom directly linked to the quaternized nitrogen atom is a carbon atom;

R'₅ borne by the quaternized nitrogen atom, in the case of W₃, represents a bond to LK;

R'₇ is chosen from optionally substituted $C_1$–$C_4$ alkyl radicals; optionally substituted phenyl radicals; and optionally substituted benzyl radicals; the bond c links the cationic radical defined by formulae (1) to (11) to the azo group; wherein the bond may be on the main or secondary ring;

p is an integer ranging from 0 to 4;

p' is an integer ranging from 0 to 2;

p" is an integer ranging from 0 to 3; and when the main ring does not bear the maximum number of substituents, then the unsubstituted position bears a nitrogen atom; and LK is chosen from saturated or unsaturated, linear or branched, cyclic or non-cyclic, aromatic or non-aromatic, optionally substituted $C_2$–$C_{40}$ hydrocarbon-based chains, bearing at least one cationic charge, optionally interrupted with at least one entity chosen from hetero atoms and groups comprising at least one hetero atom; wherein if LK is linked to W'$_5$, LK may end with at least one entity chosen from hetero atoms and groups comprising at least one hetero atom;

if LK is linked to W'$_6$, LK may end with a group comprising at least one hetero atom chosen from —CO— and —SO$_2$—; and if LK is linked to W$_3$, the bonding takes place via a carbon atom; and the electrical neutrality of the compounds is ensured by at least one cosmetically acceptable anion An.

42. The dye composition of claim 41, wherein the compound of formula (I) is present in an amount ranging from 0.001% to 20% by weight relative to the total weight of the dye composition.

43. The dye composition of claim 42, wherein the compound of formula (I) is present in an amount ranging from 0.01% to 10% by weight relative to the total weight of the dye composition.

44. The dye composition of claim 41, further comprising at least one additional direct dye, at least one oxidation base optionally combined with at least one coupler, and mixtures thereof.

45. The dye composition of claim 44, wherein the at least one additional direct dye is a cationic or nonionic dye chosen from nitrobenzene dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylmethane-based dyes, and natural dyes.

46. The composition of claim 44, wherein the at least one oxidation base is chosen from o-phenylenediamines, p-phenylenediamines, double bases, o-aminophenols, p-aminophenols, heterocyclic bases, and the acid addition salts thereof.

47. The composition of claim 44, wherein the at least one coupler is chosen from m-aminophenols, m-phenylenediamines, m-diphenols, naphthols, heterocyclic couplers, and the acid addition salts thereof.

48. The composition of claim 44, further comprising at least one oxidizing agent.

49. A process for dyeing keratin fibers, comprising:

placing in contact with wet or dry fibers, for a time sufficient to obtain the desired effect, a dye composition comprising, in a medium that is suitable for dyeing keratin fibers, at least one cationic compound of formula (I), or the acid addition salts thereof:

Dye1-LK-Dye2 (I)

in which:

Dye1 and Dye2 represent:

Dye 1:

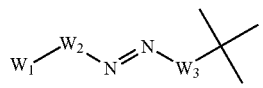

Dye 2:

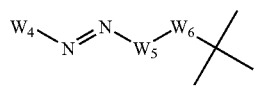

-continued

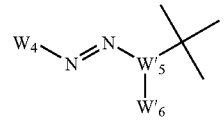

in which formulae:

W$_1$ and W'$_6$, independently of each other, are chosen from —NR$_1$R$_2$ and —OR$_3$, wherein R$_1$, R$_2$, and R$_3$, independently of each other, are chosen from hydrogen and saturated or unsaturated, aromatic or non-aromatic, optionally substituted C$_1$–C$_{20}$ hydrocarbon-based chains, which optionally form at least one optionally substituted 3- to 7-membered carbon-based ring, optionally interrupted with at least one entity chosen from hetero atoms and groups comprising at least one hetero atom;

R$_1$ and R$_2$ may optionally form, together with the nitrogen atom to which they are attached, an optionally substituted 5- or 7-membered heterocycle optionally comprising another nitrogen or non-nitrogen hetero atom; and R$_1$, R$_2$, and R$_3$, derived from W'$_6$, independently from each other, may optionally form, together with part of the group LK and the nitrogen or oxygen atom to which each is attached, a saturated or unsaturated, aromatic or non-aromatic, optionally substituted 5- to 7-membered heterocycle;

W$_6$ is chosen from —NR'$_1$— and —O—, wherein

R'$_1$ is chosen from hydrogen and saturated or unsaturated, aromatic or non-aromatic, optionally substituted C$_1$–C$_{20}$ hydrocarbon-based chains, which optionally form at least one optionally substituted 3- to 7-membered carbon-based ring, optionally interrupted with at least one entity chosen from hetero atoms and groups comprising at least one hetero atom;

R'$_1$, derived from W$_6$, may optionally form, together with the nitrogen atom to which it is attached and part of the group LK, a saturated or unsaturated, aromatic or non-aromatic, optionally substituted 5- to 7-membered heterocycle optionally containing another hetero atom chosen from nitrogen and oxygen;

W$_2$, W$_5$, and W'$_5$; independently of each other, are chosen from formulae (a), (b), and (c) below:

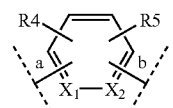

(a)

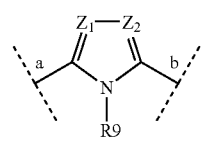

(b)

-continued

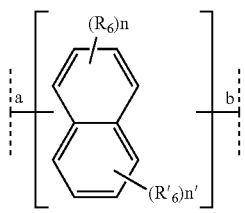

(c)

in which formulae:

$X_1$ is chosen from nitrogen and $CR_7$;
$X_2$ is chosen from nitrogen and $CR_8$;
$Z_1$ is chosen from nitrogen and $CR_{10}$; and
$Z_2$ is chosen from nitrogen and $CR_{11}$; wherein
$R_4$, $R_5$, $R_6$, $R'_6$, $R_7$, $R_8$, $R_{10}$, and $R_{11}$, independently of each other, are chosen from:
  linear or branched, saturated or unsaturated, aromatic or non-aromatic, optionally substituted $C_1$–$C_{16}$ hydrocarbon-based chains, which may form at least one optionally substituted 3- to 6-membered carbon-based ring, optionally interrupted with at least one entity chosen from hetero atoms and groups comprising at least one hetero atom;
  hydroxyl groups;
  $C_1$–$C_4$ alkoxy groups, $C_2$–$C_4$ (poly)hydroxyalkoxy groups; alkoxycarbonyl groups (RO—CO—) in which R represents a $C_1$–$C_4$ alkyl radical; alkylcarbonyloxy radicals ($R_aCO$—O—) in which $R_a$ represents a $C_1$–$C_4$ alkyl radical;
  amino groups, amino groups substituted with at least one $C_1$–$C_4$ alkyl radical, which may be identical or different, optionally comprising at least one hydroxyl group, the two alkyl radicals optionally forming, together with the nitrogen atom to which they are attached, a 5- or 6-membered heterocycle optionally comprising another nitrogen or non-nitrogen hetero atom; alkylcarbonylamino groups ($R_bCO$—$NR_b$—) in which the radicals Rb, independently of each other, are chosen fom $C_1$–$C_4$ alkyl radicals; carbamoyl groups (($R_c)_2N$—CO) in which the radicals $R_c$, independently of each other, are chosen from hydrogen and $C_1$–$C_4$ alkyl radicals; ureido groups (N($R_d)_2$—CO—NR'—) in which the radicals $R_d$ and R', independently of each other, are chosen from hydrogen and $C_1$–$C_4$ alkyl radicals; sulfonamide groups (($R_e)_2N$—$SO_2$—) in which the radicals $R_e$, independently of each other, are chosen from hydrogen and $C_1$–$C_4$ alkyl radicals; alkylsulfonylamino group ($R_fSO_2$—$NR_a'$—) in which the radicals $R_f$ and $R_a'$, independently of each other, are chosen from hydrogen and $C_1$–$C_4$ alkyl radicals; guanidinium groups (($R_h')_2N$—C(=$NH_2^+$)—$NR_g$—) in which the radicals $R_g$ and $R_h'$, independently of each other, are chosen from hydrogen and $C_1$–$C_4$ alkyl radicals;
  nitro groups; cyano groups; and halogen atoms;
$R_4$, $R_5$, $R_7$, $R_8$, $R_{10}$, and $R_{11}$ may represent hydrogen; or $R_4$, $R_5$, $R_6$, $R'_6$, $R_7$, $R_8$, $R_{10}$, and $R_{11}$, independently of each other, may optionally form, together with all or some of the groups $W_1$, $W_6$, and $W'_6$, a saturated or unsaturated, optionally substituted 5- to 7-membered heterocycle; or the bond from $W_2$ to $W_1$, from $W_5$ to $W_6$, or from $W'_5$ to $W'_6$ or to the group LK;

a represents the bond from $W_2$, $W_5$, or $W'_5$ to the azo group —N=N—;

b represents the bond from $W'_5$ to $W'_6$ or to the group LK;

$R_9$ is chosen from:
  hydrogen; and
  linear or branched, saturated or unsaturated, aromatic or non-aromatic, optionally substituted $C_1$–$C_{16}$ hydrocarbon-based chains, which may form at least one optionally substituted 3- to 7-membered carbon-based ring;

n and n' represent integers wherein the sum of n plus n' is less than or equal to 6;

$W_3$ and $W_4$, independently of each other, are chosen from cationic heteroaromatic radicals chosen from at least one of the formulae (1) to (11) below:

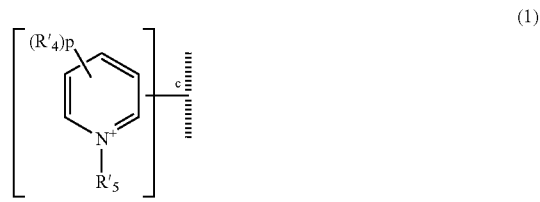

(1)

(2)

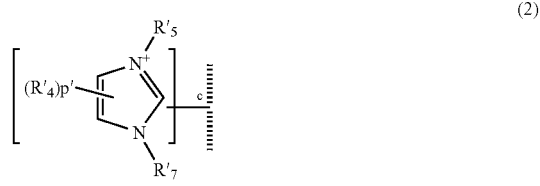

(3)

(4)

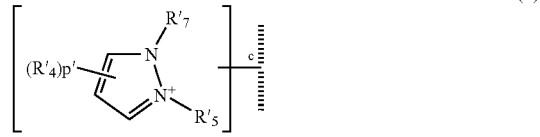

(5)

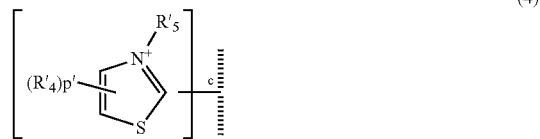

(6)

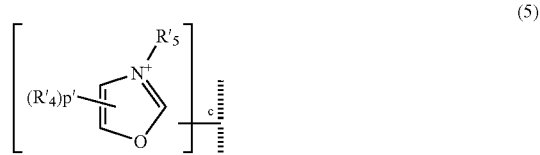

(7)

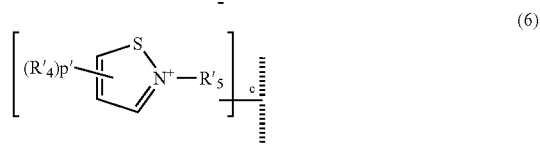

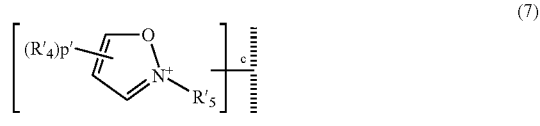

-continued

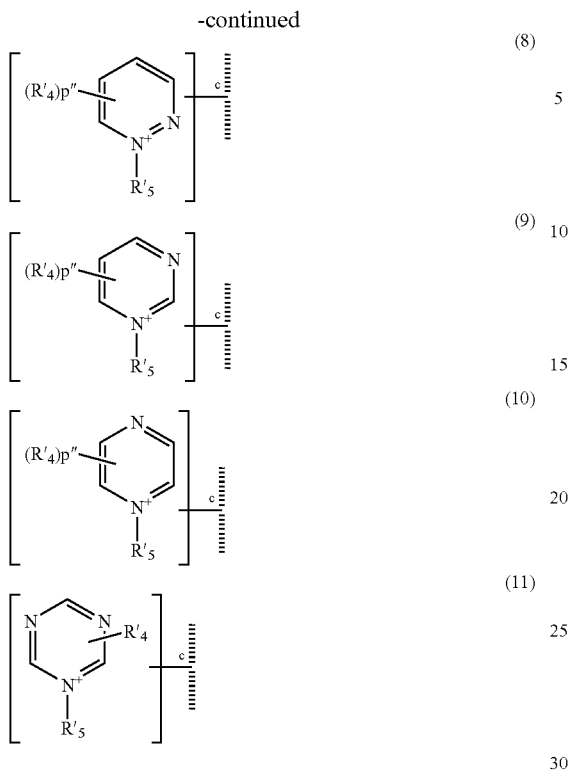

wherein:
R'₄, which may be identical or different, substituting the main ring, is chosen from:
  linear or branched, saturated or unsaturated, aromatic or non-aromatic, optionally substituted $C_1$–$C_{16}$ hydrocarbon-based chains, which may form at least one 3- to 6-membered carbon-based rings, optionally interrupted with at least one entity chosen from hetero atoms and groups comprising at least one hetero atom;
  hydroxyl groups;
  $C_1$–$C_4$ alkoxy groups, $C_2$–$C_4$ (poly)hydroxyalkoxy groups; alkoxycarbonyl groups ($R_h$O—CO—) in which $R_h$ represents a $C_1$–$C_4$ alkyl radical, alkylcarbonyloxy radicals ($R_i$CO—O—) in which $R_i$ represents a $C_1$–$C_4$ alkyl radical;
  amino groups, amino groups substituted with at least one $C_1$–$C_4$ alkyl radical, independently of each other, optionally comprising at least one hydroxyl group, the two alkyl radicals optionally forming, together with the nitrogen atom to which they are attached, a 5- or 6-membered heterocycle optionally comprising another nitrogen or non-nitrogen hetero atom; alkylcarbonylamino groups ($R_j$CO—$NR_c'$—) in which the radical $R_j$ represents a $C_1$–$C_4$ alkyl radical, and the radical $R_c'$ is chosen from hydrogen and $C_1$–$C_4$ alkyl radicals; a carbamoyl group (($R_k$)₂N—CO—) in which the radicals $R_k$, independently of each other, are chosen from hydrogen and $C_1$–$C_4$ alkyl radicals; ureido groups (N($R_L$)₂—CO—$NR_d'$—) in which the radicals $R_L$ and $R_d'$, independently of each other, are chosen from hydrogen and $C_1$–$C_4$ alkyl radicals; sulfonamide groups (($R_m$)₂N—$SO_2$—) in which the radicals $R_m$, independently of each other, are chosen from hydrogen and $C_1$–$C_4$ alkyl radicals; alkylsulfonylamino groups ($R_n SO_2$—$NR_e'$—) in which the radicals $R_n$ and $R_e'$, independently of each other, are chosen from hydrogen and $C_1$–$C_4$ alkyl radicals; guanidinium groups (($R_f'$)₂N—C(=$NH_2^+$)—$NR_p$—) in which the radicals $R_p$ and $R_f'$, independently of each other, are chosen from hydrogen and $C_1$–$C_4$ alkyl radicals;
  nitro groups; cyano groups; and halogen atoms;
  two radicals R'₄ borne by two adjacent carbon atoms of the main ring may optionally form an aromatic or non-aromatic, 5- or 6-membered secondary ring, optionally substituted with at least one entity chosen from hydrogen; hydroxyl groups; $C_1$–$C_4$ alkyl radicals; $C_1$–$C_4$ alkoxy radicals; $C_2$–$C_4$ (poly)hydroxyalkoxy radicals; amino radicals; amino radicals substituted with at least one $C_1$–$C_4$ alkyl radical, which may be identical or different, optionally comprising at least one hydroxyl group;
  R'₅, borne by the quaternized nitrogen atom, in the case of W₄, is chosen from linear or branched, saturated or unsaturated, aromatic or non-aromatic, optionally substituted $C_1$–$C_{16}$ hydrocarbon-based chains, which optionally form at least one optionally substituted 3- to 6-membered carbon-based rings, optionally interrupted with at least one entity chosen from hetero atoms and groups comprising at least one hetero atom; wherein the radical R'₅ is such that the atom directly linked to the quaternized nitrogen atom is a carbon atom;
  R'₅ borne by the quaternized nitrogen atom, in the case of W₃, represents a bond to LK;
  R'₇ is chosen from optionally substituted $C_1$–$C_4$ alkyl radicals; optionally substituted phenyl radicals; and optionally substituted benzyl radicals; the bond c links the cationic radical defined by formulae (1) to (11) to the azo group; wherein the bond may be on the main or secondary ring;
  p is an integer ranging from 0 to 4;
  p' is an integer ranging from 0 to 2;
  p" is an integer ranging from 0 to 3; and
  when the main ring does not bear the maximum number of substituents, then the unsubstituted position bears a nitrogen atom; and
  LK is chosen from saturated or unsaturated, linear or branched, cyclic or non-cyclic, aromatic or non-aromatic, optionally substituted $C_2$–$C_{40}$ hydrocarbon-based chains, bearing at least one cationic charge, optionally interrupted with at least one entity chosen from hetero atoms and groups comprising at least one hetero atom; wherein
  if LK is linked to W'₅, LK may end with at least one entity chosen from hetero atoms and groups comprising at least one hetero atom;
  if LK is linked to W'₆, LK may end with a group comprising at least one hetero atom chosen from —CO— and —$SO_2$—; and
  if LK is linked to W₃, the bonding takes place via a carbon atom; and the electrical neutrality of the compounds is ensured by at least one cosmetically acceptable anion An.

50. A multi-compartment device comprising a first compartment and a second compartment; wherein
the first compartment comprises a dye composition comprising, in a medium that is suitable for dyeing keratin fibers, at least one cationic compound of formula (I), or the acid addition salts thereof:

Dye1-LK-Dye2   (I)

in which:

Dye1 and Dye2 represent:

Dye 1:

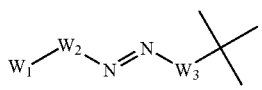

Dye 2:

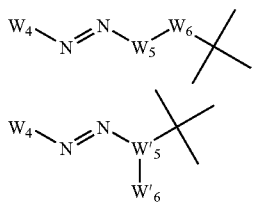

in which formulae:

$W_1$ and $W'_6$, independently of each other, are chosen from —$NR_1R_2$ and —$OR_3$, wherein $R_1$, $R_2$, and $R_3$, independently of each other, are chosen from hydrogen and saturated or unsaturated, aromatic or non-aromatic, optionally substituted $C_1$–$C_{20}$ hydrocarbon-based chains, which optionally form at least one optionally substituted 3- to 7-membered carbon-based ring, optionally interrupted with at least one entity chosen from hetero atoms and groups comprising at least one hetero atom;

$R_1$ and $R_2$ may optionally form, together with the nitrogen atom to which they are attached, an optionally substituted 5- or 7-membered heterocycle optionally comprising another nitrogen or non-nitrogen hetero atom; and $R_1$, $R_2$, and $R_3$, derived from $W'_6$, independently from each other, may optionally form, together with part of the group LK and the nitrogen or oxygen atom to which each is attached, a saturated or unsaturated, aromatic or non-aromatic, optionally substituted 5- to 7-membered heterocycle;

$W_6$ is chosen from —$NR'_1$ and —O—, wherein $R'_1$ is chosen from hydrogen and saturated or unsaturated, aromatic or non-aromatic, optionally substituted $C_1$–$C_{20}$ hydrocarbon-based chains, which optionally form at least one optionally substituted 3- to 7-membered carbon-based ring, optionally interrupted with at least one entity chosen from hetero atoms and groups comprising at least one hetero atom;

$R'_1$, derived from $W_6$, may optionally form, together with the nitrogen atom to which it is attached and part of the group LK, a saturated or unsaturated, aromatic or non-aromatic, optionally substituted 5- to 7-membered heterocycle optionally containing another hetero atom chosen from nitrogen and oxygen;

$W_2$, $W_5$, and $W'_5$, independently of each other, are chosen from formulae (a), (b), and (c) below:

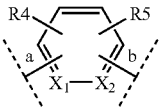

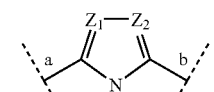

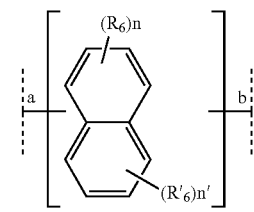

in which formulae:

$X_1$ is chosen from nitrogen and $CR_7$;

$X_2$ is chosen from nitrogen and $CR_8$;

$Z_1$ is chosen from nitrogen and $CR_{10}$; and $Z_2$ is chosen from nitrogen and $CR_{11}$; wherein $R_4$, $R_5$, $R_6$, $R_{16}$, $R_7$, $R_8$, $R_{10}$, and $R_{11}$, independently of each other, are chosen from:

linear or branched, saturated or unsaturated, aromatic or non-aromatic, optionally substituted $C_1$–$C_{16}$ hydrocarbon-based chains, which may form at least one optionally substituted 3- to 6-membered carbon-based ring, optionally interrupted with at least one entity chosen from hetero atoms and groups comprising at least one hetero atom;

hydroxyl groups;

$C_1$–$C_4$ alkoxy groups, $C_2$–$C_4$ (poly)hydroxyalkoxy groups; alkoxycarbonyl groups (RO—CO—) in which R represents a $C_1$–$C_4$ alkyl radical; alkylcarbonyloxy radicals ($R_a$CO—O—) in which $R_a$ represents a $C_1$–$C_4$ alkyl radical;

amino groups, amino groups substituted with at least one $C_1$–$C_4$ alkyl radical, which may be identical or different, optionally comprising at least one hydroxyl group, the two alkyl radicals optionally forming, together with the nitrogen atom to which they are attached, a 5- or 6-membered heterocycle optionally comprising another nitrogen or non-nitrogen hetero atom; alkylcarbonylamino groups ($R_b$CO—$NR_b$—) in which the radicals $R_b$, independently of each other, are chosen fom $C_1$–$C_4$ alkyl radicals; carbamoyl groups (($R_c$)$_2$N—CO) in which the radicals $R_c$, independently of each other, are chosen from hydrogen and $C_1$–$C_4$ alkyl radicals; ureido groups (N($R_d$)$_2$—CO—NR'—) in which the radicals $R_d$ and R', independently of each other, are chosen from hydrogen and $C_1$–$C_4$ alkyl radicals; sulfonamide groups (($R_e$)$_2$N—$SO_2$—) in which the radicals $R_e$, independently of each other, are chosen from hydrogen and $C_1$–$C_4$ alkyl radicals; alkylsulfonylamino group ($R_f SO_2$—$NR_a'$—) in which the radicals $R_f$ and $R_a'$, independently of each other, are chosen from hydrogen and $C_1$–$C_4$ alkyl radicals; guanidinium groups $((R_b')_2N\text{—}C(=NH_2^+)\text{—}NR_g\text{—})$ in which the radicals $R_g$ and $R_b'$, independently of each other, are chosen from hydrogen and $C_1$–$C_4$ alkyl radicals; nitro groups; cyano groups; and halogen atoms;

$R_4$, $R_5$, $R_7$, $R_8$, $R_{10}$, and $R_{11}$ may represent hydrogen; or $R_4$, $R_5$, $R_6$, $R_{16}$, $R_7$, $R_8$, $R_{10}$, and $R_{11}$, independently of each other, may optionally form, together with all or some of the groups $W_1$, $W_6$, and $W'_6$, a saturated or unsaturated, optionally substituted 5- to 7-membered heterocycle; or the bond from $W_2$ to $W_1$, from $W_5$ to $W_6$, or from $W'_5$ to $W'_6$ or to the group LK;

a represents the bond from $W_2$, $W_5$, or $W'_5$ to the azo group —N=N—;

b represents the bonds from $W'_5$ to $W'_6$ or to the group LK;

$R_9$ is chosen from:
hydrogen; and
linear or branched, saturated or unsaturated, aromatic or non-aromatic, optionally substituted $C_1$–$C_{16}$ hydrocarbon-based chains, which may form at least one optionally substituted 3- to 7-membered carbon-based ring;

n and n' represent integers wherein the sum of n plus n' is less than or equal to 6;

$W_3$ and $W_4$, independently of each other, are chosen from cationic heteroaromatic radicals chosen from at least one of the formulae (1) to (11) below:

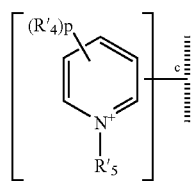
(1)

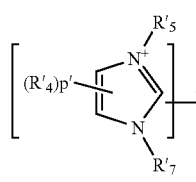
(2)

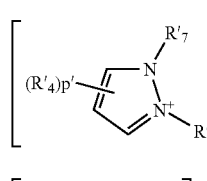
(3)

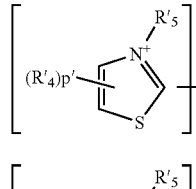
(4)

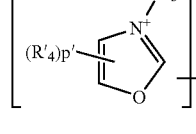
(5)

-continued

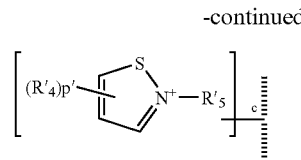
(6)

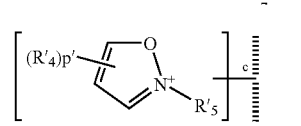
(7)

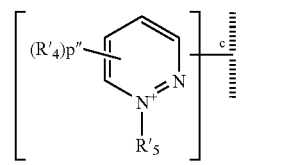
(8)

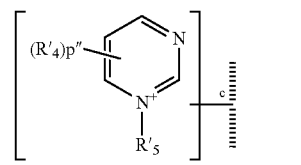
(9)

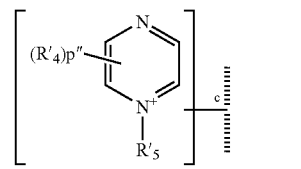
(10)

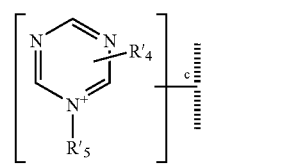
(11)

wherein:
$R'_4$, which may be identical or different, substituting the main ring, is chosen from:
linear or branched, saturated or unsaturated, aromatic or non-aromatic, optionally substituted $C_1$–$C_{16}$ hydrocarbon-based chains, which may form at least one 3- to 6-membered carbon-based rings, optionally interrupted with at least one entity chosen from hetero atoms and groups comprising at least one hetero atom;

hydroxyl groups;

$C_1$–$C_4$ alkoxy groups, $C_2$–$C_4$ (poly)hydroxyalkoxy groups; alkoxycarbonyl groups ($R_hO\text{—}CO\text{—}$) in which $R_h$ represents a $C_1$–$C_4$ alkyl radical, alkylcarbonyloxy radicals ($R_iCO\text{—}O\text{—}$) in which $R_i$ represents a $C_1$–$C_4$ alkyl radical;

amino groups, amino groups substituted with at least one $C_1$–$C_4$ alkyl radical, independently of each other, optionally comprising at least one hydroxyl group, the two alkyl radicals optionally forming, together with the nitrogen atom to which they are attached, a 5- or 6-membered heterocycle optionally comprising another nitrogen or non-nitrogen hetero atom; alkylcarbonylamino groups ($R_jCO\text{—}NR_c'\text{—}$) in which the radical $R_j$ represents a $C_1$–$C_4$ alkyl radical, and the radical $R_c'$ is chosen from hydrogen and $C_1$–$C_4$ alkyl radicals; a carbamoyl group (($R_k)_2$N—CO—) in which the radicals $R_k$, independently of each other, are chosen from hydrogen and $C_1$–$C_4$ alkyl radicals; ureido groups (N($R_L)_2$—CO—$NR_d'$—) in which the radicals $R_L$ and $R_d'$, independently of each other, are chosen from hydrogen and $C_1$–$C_4$ alkyl radicals; sulfonamide groups (($R_m)_2$N—$SO_2$—) in which the radicals $R_m$, independently of each other, are chosen from hydrogen and $C_1$–$C_4$ alkyl radicals; alkylsulfonylamino groups ($R_n SO_2$—$NR_e'$—) in which the radicals $R_n$ and $R_e'$, independently of each other, are chosen from hydrogen and $C_1$–$C_4$ alkyl radicals; guanidinium groups (($R_f')_2$N—C(=$NH_2^+$)—$NR_p$—) in which the radicals $R_p$ and $R_f'$, independently of each other, are chosen from hydrogen and $C_1$–$C_4$ alkyl radicals;

nitro groups; cyano groups; and halogen atoms;

two radicals $R_4'$ borne by two adjacent carbon atoms of the main ring may optionally form an aromatic or non-aromatic, 5- or 6-membered secondary ring, optionally substituted with at least one entity chosen from hydrogen; hydroxyl groups; $C_1$–$C_4$ alkyl radicals; $C_1$–$C_4$ alkoxy radicals; $C_2$–$C_4$ (poly)hydroxyalkoxy radicals; amino radicals; amino radicals substituted with at least one $C_1$–$C_4$ alkyl radical, which may be identical or different, optionally comprising at least one hydroxyl group;

$R_5'$, borne by the quaternized nitrogen atom, in the case of $W_4$, is chosen from linear or branched, saturated or unsaturated, aromatic or non-aromatic, optionally substituted $C_1$–$C_{16}$ hydrocarbon-based chains, which optionally form at least one optionally substituted 3- to 6-membered carbon-based rings, optionally interrupted with at least one entity chosen from hetero atoms and groups comprising at least one hetero atom; wherein the radical $R_5'$ is such that the atom directly linked to the quaternized nitrogen atom is a carbon atom;

$R_5'$ borne by the quaternized nitrogen atom, in the case of $W_3$, represents a bond to LK;

$R_7'$ is chosen from optionally substituted $C_1$–$C_4$ alkyl radicals; optionally substituted phenyl radicals; and optionally substituted benzyl radicals; the bond c links the cationic radical defined by formulae (1) to (11) to the azo group; wherein the bond may be on the main or secondary ring;

p is an integer ranging from 0 to 4;

p' is an integer ranging from 0 to 2;

p" is an integer ranging from 0 to 3; and when the main ring does not bear the maximum number of substituents, then the unsubstituted position bears a nitrogen atom; and LK is chosen from saturated or unsaturated, linear or branched, cyclic or non-cyclic, aromatic or non-aromatic, optionally substituted $C_2$–$C_{40}$ hydrocarbon-based chains, bearing at least one cationic charge, optionally interrupted with at least one entity chosen from hetero atoms and groups comprising at least one hetero atom; wherein if LK is linked to $W_5'$, LK may end with at least one entity chosen from hetero atoms and groups comprising at least one hetero atom;

if LK is linked to $W_6'$, LK may end with a group comprising at least one hetero atom chosen from —CO— and —$SO_2$—; and if LK is linked to $W_3$, the bonding takes place via a carbon atom; and the electrical neutrality of the compounds is ensured by at least one cosmetically acceptable anion An; and the second compartment comprises an oxidizing composition.

\* \* \* \* \*

UNITED STATES PATENT AND TRADEMARK OFFICE
CERTIFICATE OF CORRECTION

PATENT NO. : 7,208,586 B2
APPLICATION NO. : 11/159267
DATED : April 24, 2007
INVENTOR(S) : Andrew Greaves and Hervé David It is certified that error appears in the above-identified patent and that said Letters Patent is hereby corrected as shown below:

In Claim 41, col. 48, line 26, "$R_g$" should read --$R_9$--.

Signed and Sealed this

Twenty-sixth Day of June, 2007

JON W. DUDAS
*Director of the United States Patent and Trademark Office*